United States Patent [19]

Stec et al.

[11] Patent Number: 5,856,465

[45] Date of Patent: Jan. 5, 1999

[54] COMPOSITIONS AND METHODS FOR THE SYNTHESIS OF CHIRALLY PURE ORGANOPHOSPHORUS NUCLEOSIDE DERIVATIVES

[75] Inventors: Wojciech Jacek Stec, Ksawerow; Lucyna Wozniak, Lodz, both of Poland

[73] Assignee: Polska Akademia Nauk Centrum Badan Molekularnych I Makromolekularnych, Lodz, Poland

[21] Appl. No.: 704,975

[22] Filed: Aug. 29, 1996

Related U.S. Application Data

[63] Continuation-in-part of Ser. No. 653,204, May 26, 1996.

[51] Int. Cl.⁶ .............................. C07H 21/00; C07H 1/00
[52] U.S. Cl. .................. 536/25.3; 536/25.31; 536/25.32; 536/25.34; 536/25.4; 536/25.41; 536/124; 536/125; 536/126

[58] Field of Search .................. 536/253, 25.31, 536/25.32, 25.34, 25.4, 25.41, 124, 125, 126

[56] References Cited

U.S. PATENT DOCUMENTS 5,359,052 10/1994 Stec et al. .
5,512,668 4/1996 Stec et al. .
5,646,267 7/1997 Stec et al. .

*Primary Examiner*—James O. Wilson
*Attorney, Agent, or Firm*—Knobbe, Martens, Olson & Bear, LLP

[57] ABSTRACT

Methods for the stereospecific synthesis of chirally pure organophosphorus dinucleotide derivatives and nucleoside monomer synthons used in their synthesis are provided. These methods allow for conversion of nucleoside intermediates of unchosen sense of P-chirality to nucleoside monomer synthons of chosen sense of P-chirality. Also provided are novel nucleoside intermediates useful in such methods.

16 Claims, 4 Drawing Sheets

Formula I

Formula II

Formula III

Formula IV

Formula V

Formula VI

COMPOSITIONS AND METHODS FOR THE SYNTHESIS OF CHIRALLY PURE ORGANOPHOSPHORUS NUCLEOSIDE DERIVATIVES

CROSS REFERENCE TO RELATED APPLICATIONS

This application is a continuation-in-part of U.S. Ser. No. 08/653,204 filed May 26, 1996 and claims priority from the following Polish patent applications: Polish patent application Serial No. P-310248 filed Aug. 31, 1995 and Polish patent application Serial No. P-312934 filed Feb. 26, 1996.

TECHNICAL FIELD

The present invention relates generally to novel organophosphorus mono- and di- nucleoside derivatives and methods for their synthesis.

BACKGROUND OF THE INVENTION

It is well known that most of the bodily states in animals, including disease states, are effected by proteins. Such proteins, either acting directly or through their enzymatic functions contribute to many disease states in animals and man.

Classical therapeutics have generally focused upon interactions with such proteins in an effort to moderate their disease causing or disease potentiating functions. Recently, however, attempts have been made to moderate the biosynthesis of such proteins by interactions with the molecules (i.e. intercellular RNA) that direct their synthesis. These interactions have involved the hybridization of complementary "antisense" oligonucleotides or certain analogs thereof to RNA. Hybridization refers to the sequence-specific hydrogen bonding of oligonucleotides or oligonucleotide analogs to RNA or DNA. When hybridization occurs biosynthesis of proteins can be interrupted. This interference with the production of proteins, has been expected to effect therapeutic results with maximum effect and minimal side effects. Oligonucleotide analogs may also be utilized to moderate the production of proteins by a similar mechanism.

The pharmacological activity of antisense oligonucleotides and oligonucleotide analogs, like other therapeutics, depends on a number of factors that influence the effective concentration of these agents at specific intercellular targets. One important factor for oligonucleotides is the stability of the species in the presence of nucleases. It is rather unlikely that unmodified oligonucleotides will be useful therapeutic agents because they are rapidly degraded by nucleases. Modifications of oligonucleotides to render them resistant to nucleases therefore are greatly desired.

Modifications of oligonucleotides to enhance nuclease resistance have generally taken place on the phosphorus atom of the sugar-phosphate backbone. Phosphorothioates, methyl phosphonates, phophoramidates, and phosphorotriesters have been reported to confer various levels of nuclease resistance. However, phosphate-modified oligonucleotides of this type generally have suffered from inferior hybridization properties (Cohen, J. S., ed. *Oligonucleotides: Antisense Inhibitors of Gene Expression*, CRC Press, Inc. Boca Raton Fla., 1989)

Another key factor is the ability of antisense compounds to traverse the plasma membrane of specific cells involved in the disease process. Cellular membranes consist of lipid-protein bilayers that are easily permeable to small, nonionic, lipophilic compounds yet inherently impermeable to most natural metabolites and therapeutic agents (Wilson, D. B. *Ann. Rev. Biochem.* 47:933, 1978) The biological and antiviral effects of natural and modified oligonucleotides in cultured mammalian cells have been well documented. Thus, it appears that these agents can penetrate membranes to reach their intercellular targets. Uptake of antisense compounds by a variety of mammalian cells including HL-60, Syrian Hamster fibroblast, U937, L929, CV-1 and ATH8 cells, have been studied using natural oligonucleotides and certain nuclease resistant analogs, such as alkyl triesters (Miller P. S. et al., *Biochem.* 16:1988, 1977); methylphosphonates (Marcus-Sekura, C. H. et al., *Nuc. Acids Res.* 15:5749, 1987; Miller P. S. et al., *Biochem.* 16:1988, 1977; and Loke S. K. et al., *Top. Microbiol. Immunol.* 141:282, 1988).

Modified oligonucleotides and oligonucleotide analogs may be less readily internalized than their natural counterparts. As a result, the activity of many previously available antisense oligonucleotides have not been sufficient for practical therapeutic, research or diagnostic purposes. Two other deficiencies recognized by the prior art are that many of the previously designed oligonucleotide antisense therapeutics hybridize less efficiently to intercellular RNA and lack the defined chemical or enzyme-mediated event to terminate essential RNA function.

Modifications to enhance the effectiveness of the antisense oligonucleotides and overcome these problems have taken many forms. These modifications include base ring modifications, sugar moiety modifications, and sugar-phosphate backbone modifications. Prior sugar-phosphate backbone modifications, particularly on the phosphorus atom, have effected various levels of resistance to nucleases. However, while the ability of an antisense oligonucleotide to bind with fidelity to specific DNA or RNA is fundamental to antisense methodology, modified phosphorus oligonucleotides have generally suffered from inferior hybridization properties.

Replacement of the phosphorus atom has been an alternative approach in attempting to avoid the problems associated with modification on the prochiral phosphate moiety. Some modifications in which replacement of the phosphorus atom has been achieved are discussed by Matteucci, (*Tetrahedron Letters* 31:2385, 1990), wherein replacement of the phosphorus atom with a methylene group is limited by available methodology which does not provide for uniform insertion of the formacetal linkage throughout the backbone, and its instability, making it unsuitable for use; Cormier, (*Nuc. Acids Res.* 16:4583, 1988), wherein replacement of the phosphorus moiety with a diisopropylsilyl moiety is limited by methodology, solubility of the homopolymers and hybridization properties; Stirchak (*J. Org. Chem.* 52:4202, 1987), wherein replacement of the phosphorus linkage by short homopolymers containing carbamate or morpholino linkages is limited by methodology, the solubility of the resulting molecule, and hybridization properties; Mazur (*Tetrahedron* 40:3949, 1984), wherein replacement of the phosphorus linkage with a phosphonic linkage has not been developed beyond the synthesis of a homotrimer molecule; and Goodrich (*Bioconj. Chem.* 1:165, 1990) wherein ester linkages are enzymatically degraded by esterases and are therefore unsuitable to replace the phosphate bond in antisense applications.

Another key factor are the stereochemical effects that arise in oligomers having P-chiral centers. In general, an oligomer with a length of n nucleosides will constitute a mixture of $2^{n-1}$ isomers in successive non-stereospecific chain synthesis.

It has been observed that Rp and Sp homochiral chains, whose absolute configuration at all internucleotide methanephosphonate phosphorus atoms is either Rp or Sp, and non-stereoregular chains show different physicochemical properties as well as different capabilities of forming adducts with oligonucleotides of complementary sequence. In addition, phosphorothioate analogs of nucleotides have shown substantial stereoselectivity differences between Oligo-Rp and Oligo-Sp oligonucleotides in resistance to nucleases activity (Potter, *Biochemistry*, 22:1369, 1983; Bryant et al., *Biochemistry*, 18:2825, 1979).

Lesnikowski (*Nucl. Acids Res.*, 18:2109, 1990 observed that diastereomerically pure octathymidine methylphosphonates, in which six out of seven methylphosphonate bonds have defined configuration at the phosphorus atom when complexed with the matrix of pentadecadeoxyriboadenylic acid show substantial differences in melting temperatures. The Oligonucleotide compounds with predetermined configuration at the phosphorus atom, used in these studies, were prepared by the stereocontrolled process between the 5'-hydroxyl nucleoside group activated by means of the Grignard's reagent, and the diastereomerically pure nucleoside p-nitrophenylmethylphosphonate (Lesnikowski et al., *Nucl. Acids Res.*, 18:2109, 1990; Lesnikowski et al., *Nucleosides & Nucleotides*, 10:773, 1991; Lesnikowski, *Nucl. Acids Res.*, 16:11675, 1988). This method, however, requires long reaction time, and has been verified only in the case of the synthesis of tetramer homothymidine fragments and heteromeric hexamers.

Attempts to prepare diastereomerically pure oligomethylphosphonate compounds by reacting at low temperatures (−80° C.) with methyldichlorophosphine and appropriate nucleosides protected at 5' or 3' positions, resulted in the formation of Rp isomers of relevant dinucleoside methylphosphonates at a maximum predominance of 8:1 (Loschner, *Tetrahedron Lett.*, 30:5587, 1989; and Engels et al., *Nucleosides & Nucleotides*, 10:347, 1991).

However, longer stereoregular chains cannot be prepared by this method because intermediate nucleoside 3'-O-P-chloromethylphosphonites, formed during the condensation, have a labile configuration even at low temperatures.

The limitations of the available methods for modification and synthesis of the organophosphorus derivatives have led to a continuing and long felt need for other modifications which provide resistance to nucleases and satisfactory hybridization properties for antisense oligonucleotide diagnostics, therapeutics, and research.

SUMMARY OF THE INVENTION

The present invention is directed to methods of synthesizing chirally pure nucleoside synthons of chosen sense of P-chirality and of coupling the chirally pure synthons in a stereospecific manner to give nucleoside dimers having chosen sense of P-chirality at the internucleotide phosphorus.

As noted above, phosphodiester internucleoside linkages have no chiral center at the phosphorus atom. However, internucleoside linkages, such as alkyl and arylphosphonates, have chiral centers at the phosphorus atom by virtue of asymmetry of the phosphorus atom.

Therefore, oligonucleotide analogs containing an internucleoside alkylphosphonate or arylphosphonate linkages consist of a mixture of $2^n$ diastereomers, if the process of internucleoside bond formation is nonstereospecific. Since one or a population of oligonucleotide analogs of Rp or Sp sense of chirality at phosphorus generally possess preferred properties, such as higher binding affinity to its complementary target sequence, one of the stereoisomers will generally be preferred. Conventional synthetic techniques provide nucleotide dimers and other oligonucleotides having chiral center(s) at the internucleoside linkage(s) as a racemic mixture (in about a 50/50 ratio at each P-chiral center) from which the desired diastereomer is separated by techniques such as chromatography. The undesired diastereomer is typically discarded as a side product. As one should appreciate, loss of about 50% of the product per coupling step by formation of the diastereomer of unchosen sense of P-chirality will greatly reduce yields and, in view of the expense of many nucleoside monomer synthons, will also result in high cost of the synthesis product.

Among other factors, the present invention is based on our finding that use of our synthetic methods allows for substantially higher conversion of nucleoside starting materials into chirally pure nucleoside monomer synthons of the chosen sense of P-chirality. Thus, in one aspect the present invention is directed to a new synthetic methods for producing chirally pure nucleoside monomer synthons of chosen sense of P-chirality and their use in a stereospecific coupling reaction to yield nucleotide dimers of the chosen sense of P-chirality. Also provided are synthetic methods for converting nucleoside intermediates of the unchosen sense of P-chirality into nucleoside monomer synthons of the chosen sense of P-chirality for use in the above-noted stereospecific coupling reaction. Thus, by use of the synthetic methods of the present invention, substantially all of the nucleoside starting material may be converted into chirality pure nucleoside monomer synthons of the chosen sense of P-chirality and then used to obtain chirally pure nucleotide dimers with little waste of nucleoside starring material. Further coupling of the chirally pure nucleoside monomer synthons will yield chirally pure oligonucleotides. Accordingly, our synthetic methods offer advantages which include more efficient use of starting materials and substantially higher yields of chirally pure and/or chirally enriched oligonucleosides.

Thus, according to one aspect of the present invention, methods are provided for the synthesis of chirally pure nucleotide dimers of chosen sense of P-chirality of formula I (these formulas are depicted in FIGS. 1 to 4) wherein (a) $R_1$ is a protecting group;

(b) each $R_2$ is independently selected from hydrogen, optionally protected hydroxy, halogen, chloroalkyl or fluoroalkyl of 1 to 4 carbon atoms and 1 to 9 chlorine or fluorine atoms, cyano, azido, optionally protected amino, perfluoroalkyl of 1 to 4 carbon atoms, perfluoroalkoxy of 1 to 4 carbon atoms, alkoxyalkyl, vinyl, ethynyl -$Q_1$, -$OQ_1$, -$SQ_1$ or -$NHQ_1$ wherein -$Q_1$ is alkyl of 1 to 12 carbon atoms, aryl of 1 to 12 carbon atoms, aralkyl of 2 to 15 carbon atoms, alkaryl of 2 to 15 carbon atoms, alkenyl of 3 to 12 carbon atoms, and alkynl of 3 to 12 carbon atoms.

(c) B is an independently selected optionally protected nucleoside base;

(d) Z is independently selected from -$Q_1$, vinyl, ethynyl, optionally protected aminomethyl and optionally protected aminoethyl; and (e) $R_X$ is an aroyl protecting group, acyl protecting group, alkoxycarbonyl protecting group, benzenesulfonyl or ring-substituted benzenesulfonyl protecting group, a coupling group, a silyl protecting group such as a t-butyldimethylsilyl group, a 5'-O-nucleotide analog, a 5'-O-oligonucleotide analog or an alkyl protecting group.

This method comprises separation of a racemic mixture of the compound of formula II into diastereomers of chosen and unchosen sense of P-chirality wherein $R_1$, $R_2$, B, and Z are as defined in connection with formula I and wherein X is sulfur or selenium and Ar is phenyl optionally substituted with 1 to 5 substituents independently selected from halogen, nitro, cyano and lower alkyl of 1 to about 6 carbon atoms. The diastereomer of formula II of chosen sense of P-chirality ("IIC") is reacted with a strong non-nucleophilic base such as potassium t-butoxide, sodium hydride or 1,8-diazabicyclo[5.4.0]undec-7-ene ("DBU"), preferably sodium hydride or DBU, and carbon dioxide to form a transient nucleoside 3'-O-(Z-substituted) phosphonoselenoic or phosphonothioic acid intermediate which is then reacted to add the $R_3$-group with an alkylating agent of the formula $R_3W$ wherein W is selected from chloro, bromo, iodo, alkanesulfonyl, perfluoroalkanesulfonyl, triflate, tosylate, mesytilate, triisopropyl benzenesulfonyl or benzenesulfonyl and $R_3$ is $-Q_1$ to give a chirally pure diastereomer of chosen sense of P-chirality of formula III ("IIIC") wherein $R_1$, $R_2$, $R_3$, B, Z, and X are as defined above. The diastereomer of formula II of unchosen sense of P-chirality ("IIUC") is converted into a chirally pure nucleoside monomer synthon of chosen sense of P-chirality of formula III ("IIIC") by first reacting compound IUC with an oxygen transferring oxidizing agent to give an intermediate nucleoside of unchosen sense of P-chirality of formula IV, then reacting the intermediate of formula IV ("IVUC") with a strong non-nucleophilic base such as potassium t-butoxide, sodium hydride or DBU, preferably sodium hydride or DBU, and $CX_2$ wherein X is sulfur or selenium to give a transient nucleoside 3'-O-(Z-substituted) phosphonoselenoic or phosphonothioic acid intermediate and then reacting the transient intermediate with an alkylating agent $R_3W$ wherein $R_3$ and W are as defined above to give a chirally pure diastereomer of chosen sense of P-chirality of formula III ("IIIC"). The chirally pure nucleoside monomer synthon of chosen sense of P-chirality of formula III ("IIIC") is then coupled with a nucleoside of formula V wherein $R_2$, $R_X$ and B are as defined hereinabove under stereospecific coupling conditions, including an activator, preferably DBU, and a lithium halide salt to give the chirally pure dimer of chosen sense of P-chirality of formula I.

According to an alternate aspect, the present invention provides certain novel intermediates and nucleoside monomer synthons.

Thus, novel intermediates of formula II are provided wherein $R_1$, $R_2$, B, X, Z and Ar are as set forth above, with the proviso that when Ar is unsubstituted phenyl, then $R_2$ is not hydrogen.

Preferred intermediates of formula II include those compounds wherein Ar is substituted. Such compounds will exhibit increased crystallinity which may allow for separation of diastereomers of chosen and unchosen sense of P-chirality by fractional crystallization. Also, compounds having substituted Ar groups may exhibit modified chromatographic behavior and thus, exhibit characteristics which allow for better separation of diastereomers by chromatographic means.

Also novel intermediates of formula IV are provided wherein $R_1$, $R_2$, B, Z and Ar are as defined above.

Novel nucleoside monomer synthons of formula III are provided wherein $R_1$, $R_2$, $R_3$, B, Z and X are as defined hereinabove with the proviso that when $R_2$ is hydrogen, optionally protected hydroxyl or methoxy, then $R_3$ is not methyl, benzyl or nitrobenzyl.

DEFINITIONS

Prior to setting forth the invention, it may be helpful to an understanding thereof to first set forth definitions of certain terms that will be used hereinafter. These terms have the following meaning unless expressly stated to the contrary.

The term "alkyl" refers to saturated aliphatic groups including straight-chain, branched-chain and cyclic groups. Suitable alkyl groups include cyclohexyl and cyclohexylmethyl. "Lower alkyl" refers to alkyl groups of 1 to 6 carbon atoms.

The term "aryl" refers to aromatic groups which have at least one ring having a conjugated pi electron system and includes carbocyclic aryl, heterocyclic aryl and biaryl groups, all of which may be optionally substituted.

The term "carbocyclic aryl" refers to aromatic groups wherein the ring atoms on the aromatic ring are carbon atoms. Carbocyclic aryl groups include monocyclic carbocyclic aryl groups and naphthyl groups, all of which may be optionally substituted. Suitable carbocylic aryl groups include phenyl and naphthyl.

The term "aromatic heterocycle" refers to aromatic groups having from 1 to 3 heteroatoms as ring atoms in the aromatic ring and the remainder of the ring atoms are carbon atoms. Suitable heteroatoms include oxygen, sulfur, and nitrogen, and suitable heterocyclic aryls include furanyl, thienyl, pyridyl, pyrroilyl, pyrimidyl, pyrazinyl, imidazolyl, and the like.

The term "biaryl" refers to phenyl substituted by carbocyclic or heterocyclic aryl as defined herein, ortho, meta or para to the point of attachment of the phenyl ring, advantageously para.

The term "lower" referred to herein in connection with organic radicals or compounds defines such with up to and including 6, preferably up to and including 4 and advantageously one or two carbon atoms. Such groups may be straight chain or branched chain.

The term "alkoxy" refers to -OR wherein R is alkyl.

The term "aralkyl" refers to an alkyl group substituted with an aryl group. Suitable aralkyl groups include benzyl, picolyl, and the like, all of which may be optionally substituted.

The term "alkaryl" refers to an aryl group that is substituted with an alkyl group. Typical alkaryl groups include cumenyl, tolyl and the like.

The term "cycloalkyl" refers to a cyclic alkyl group. Suitable cycloalkyl groups include cyclohexyl.

The term "alkenyl" refers to an unsaturated aliphatic group having at least one double bond.

The term "alkylene" refers to a divalent straight chain or branched chain saturated aliphatic radical.

The term "nucleoside base" refers to adenine, guanine, cytosine, thymidine, uracil as well as analogs and modified forms of naturally-occurring bases, including the pyrimidine-analogs such as pseudoisocytosine and pseudouracil, and other modified bases such as 8-substituted purines.

The term "Z-substituted" refers to a reagent or reactant which contains the Z substituent wherein Z is defined as set forth in connection with formulas I to IV herein, and the reagent or reactant is that specified, for example, dichlorophosphine, phosphonothioic acid, phosphonoselenoic acid, phosphonoanilidoselenoate, or phosphonoanilidothioate.

The term "nucleoside" as used in the terms "mononucleoside", "dinucleoside", and oligonucleoside refers to a subunit of a nucleic acid which comprises a 5-carbon sugar and a nitrogen-containing base. The term includes not only those nucleosidyl units having adenine, guanine, cytosine, thimidine and uracil, as their bases but also analogs and modified forms of naturally-occurring bases, including the pyrimidine analogs such as pseudoisocytosine and pseudouracil, and other modified bases such as 8-substituted purines. In RNA, the 5-carbon sugar is ribose; in DNA the 5-carbon sugar is deoxyribose. The term nucleoside also includes other analogs of such subunits, including those which have modified sugars such as 2'-O-alkyl ribose for example. The prefix of "mono", "di", and "oligo" refer to the number of nucleosides present. "Mono" means one and refers to a single nucleoside, "di" means two and refers to a compound comprising two nucleosides, and, "oligo" means many and refers to a compound with multiple nucleosides.

The "nucleotide" as used herein and in such terms as "dinucleotide" and oligonucleotide refers to the subunit of a nucleic acid which comprises a nucleoside and a phosphoric or phosphonic acid or derivative or analog thereof.

The term "purine" or "purine base" includes not only the naturally occurring adenine and guanine bases, but also modifications of those bases such as bases substituted at the 8-position, or guanine analogs modified at the 6-position or the analog of adenine, 2-amino purine, as well as analogs of purines having carbon replacing nitrogen at the 9-position such as the 9-deaza purine derivatives and other purine analogs.

The term "pyrimidine" or pyrimidine base", includes not only the naturally occurring cytosine, uracil and thymine but also modifications to these bases such as 5-propymyluracil, 5-heteroaryluracils and analogs of pyrimidines such as reported heteroaromatic moieties.

The term "phosphonate" refers to the group

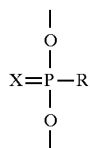

wherein X is oxygen or sulfur, R is hydrogen or an alkyl or aryl group, and thus includes various examples of phosphonate and phosphonothioate internucleosidyl linkages.

A "non-nucleoside monomeric unit" refers to a monomeric unit wherein the base, the sugar and/or the phosphorus backbone has been replaced by other chemical moieties.

A "nucleoside/non-nucleoside polymer" refers to a polymer comprised of nucleoside and non-nucleoside moneric units.

The term "oligonucleoside" or Oligomer" refers to a chain of nucleosides which are linked by internucleoside linkages which is generally from about 4 to about 100 nucleosides in length, but which may be greater than about 100 nucleosides in length. They are usually synthesized from nucleoside monomers, but may also be obtained by enzymatic means. "Oligomers" include oligonucleotides as well as oligonucleosides which contain non-phosphorus internucleosidyl linkages. Thus, the term "Oligomer" refers to a chain of oligonucleosides which have internucleosidyl linkages linking the nucleoside monomers and, thus, includes oligonucleotides, nonionic oligonucleoside alkyl- and aryl-phosphonate analogs, alkyl- and aryl-phosphonothioates, phosphorothioate or phosphorodithioate analogs of oligonucleotides, neutral phosphate ester oligonucleoside analogs, such as phosphotriesters and other oligonucleoside analogs and modified oligonucleosides, and also includes nucleoside/non-nucleoside polymers. The terms also includes nucleoside/non-nucleoside polymers wherein one or more of the phosphorus group linkages between monomeric units has been replaced by a non-phosphorous linkage such as a formacetal linkage, a thioformacetal linkage, a sulfamate linkage, or a carbamate linkage. It also includes nucleoside/non-nucleoside polymers wherein both the sugar and the phosphorous moiety have been replaced or modified such as morpholino base analogs, or polyamide base analogs. It also includes nucleoside/non-nucleoside polymers wherein the base, the sugar, and the phosphate backbone of the non-nucleoside are either replaced by a non-nucleoside moiety or wherein a non-nucleoside polymer. Optionally, said non-nucleoside moiety may serve to link other small molecules which may interact with target sequences or alter uptake into target cells.

DETAILED DESCRIPTION OF THE INVENTION

A. Preferred Methods of Synthesis

The present invention provides methods for the synthesis of chirally pure dinucleotides of chosen sense of P-chirality, and for oligorucleotides which are chirally pure or chirally enriched for a chosen sense of P-chirality. By successively coupling such chirally pure dinucleotides, chirally enriched oligonucleotides may be prepared. Alternatively, chirally pure nucleoside monomer synthons may be sequentially coupled to a dinucleotide of formula I (which forms part of a growing oligonucleotide chain), after removal of protecting group $R_1$, under stereospecific coupling conditions similar to those used for the coupling reaction depicted in FIG. 2 to give a oligonucleotide of desired length. In addition, the chirally pure nucleoside monomer synthons may be coupled to an oligomer having a mixture of internucleosidyl linkages, including non-phosphorus internucleosidyl linkages.

Figure 3:
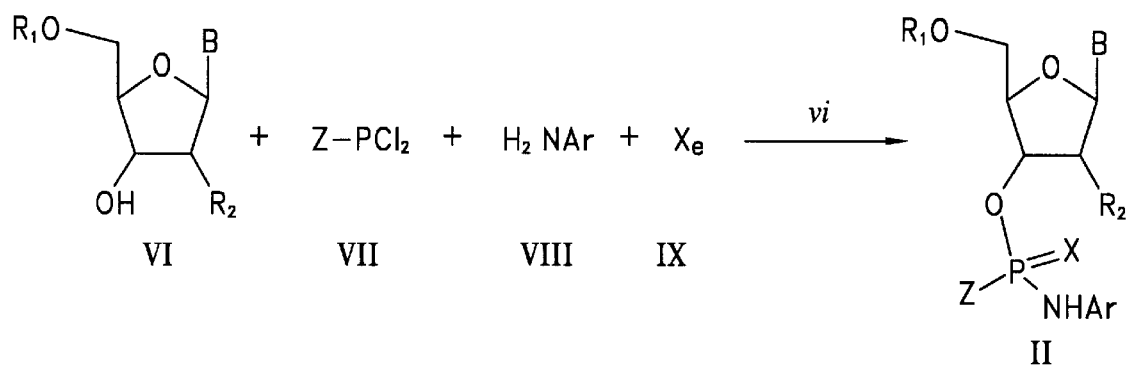
FIG. 3 depicts a synthetic scheme for the preparation of nucleoside anilidate intermediates according to the present invention. In this figure, $X_8$ represents elemental sulfur or selenium.
Figure 4:
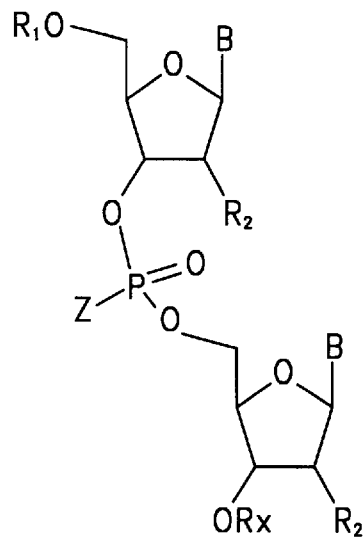
FIG. 4 depicts the structures of the compounds of formulas I to VI.
Figure 4:
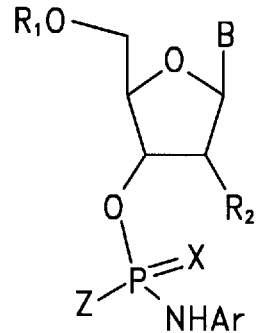
Figure 4:
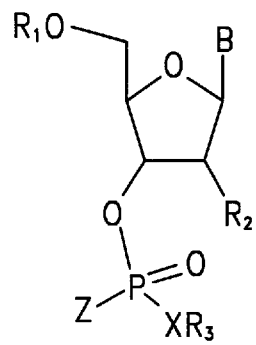
Figure 4:
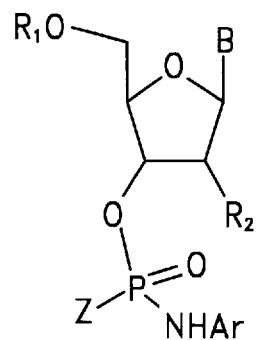
Figure 4:
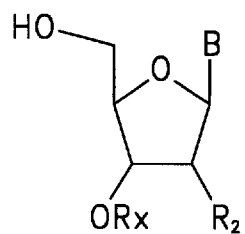
Figure 4:
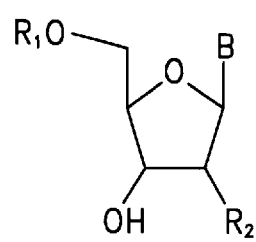

FIG. 3 depicts a method of preparing nucleoside anilidate intermediates of formula II. The starting 5'-protected, 3-OH nucleoside is reacted with a Z-substituted dichlorophosphine, Z-PCl$_2$), and an optionally substituted aniline (H$_2$NAr) and either elemental sulfur or selenium. The reaction is conducted in an inert organic solvent. Suitable solvents include chloroalkanes (such as dichloromethane), aprotic polar solvents such as tetrahydrofuran (THF), acetonitrile (MeCN) and other inert organic solvents such as toluene, xylenes and the like. The reaction is conveniently conducted at ambient temperature. Preferably the reaction is conducted under N$_2$. These intermediates of formula II are prepared as a racemic mixture.

Figure 1:
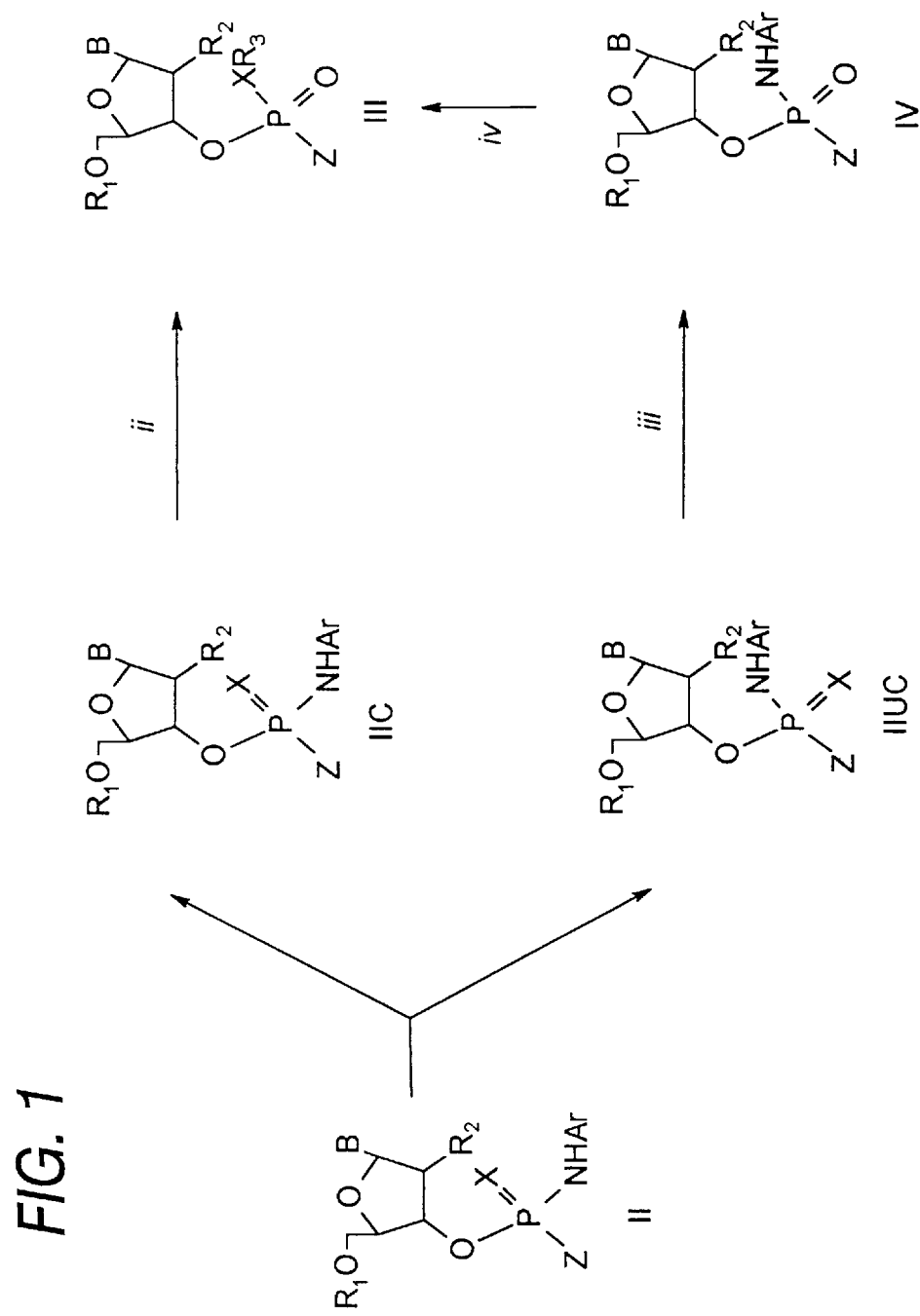
FIG. 1 depicts a synthesis scheme for the preparation of chirally pure nucleoside monomer synthons of chosen sense of P-chirality according to the present invention. In this figure, the compounds of formulas I, II, III and V are as defined in the Detailed Description of the Invention. In this figure, i) is defined as means of separating of compound (II) into diastereomers (IIC) and (IIUC). Compound (IIC) represents the diastereomer of chosen sense of P-chirality. Diastereomer (IIUC) represents the diastereomer of unchosen sense of P-chirality. Also in this figure, ii) represents sodium hydride or 1,8-diazabizyclo[5.4.0]undec-7-ene ("DBU") and carbon dioxide followed by alkylating agent $R_3W$; iii) represents an oxygen transferring oxidizing agent and iv) represents sodium hydride or DBU and $CX_2$, where X is sulfur or selenium.

FIG. 1 depicts the preparation of chirally pure nucleoside monomer synthons of chosen sense of P-chirality using the intermediates of formula II. According to this method, the intermediates of formula II which are prepared as a mixture of diastereomers of P-chirality are separated into diastereomers of chosen sense of P-chirality and unchosen sense of P-chirality. The diastereomers may be separated by conventional techniques, including chromatography. Example 11 describes one such separation.

The diastereomer of chosen sense of P-chirality, compound IIC, is converted to compound III, a nucleoside monomer synthon of chosen sense of P-chirality by reacting it with sodium hydride or DBU and carbon dioxide to give a transient nucleoside 3'-O-(Z-substituted phosphonoselenoic or phosphonothioic acid intermediate and then contacting the transient intermediate so formed with an alkylating agent of the formula R$_3$W to give compound III.

Compound IIUC, the nucleoside intermediate of unchosen sense of P-chirality, is converted to compound III, a nucleoside monomer synthon of chosen sense of P-chirality as set forth in FIG. 1. Compound IIUC is reacted with an oxygen transferring oxidizing agent to form nucleoside intermediate IV. Suitable oxygen transferring oxidizing agents include oxone, hydroperoxide, alkylhydroperoxides, arylhydroperoxides, perbenzoic acids and perphthalates. The intermediate of formula IV is then reacted with sodium hydride or DBU and CX$_2$ (where X is sulfur or selenium) to give a transient nucleoside 3'-O-(Z-substituted) phosphonoselenoic or phosphonothioic acid intermediate. The transient intermediate formed thereby is then reacted with an alkylating agent of formula R$_3$W to give the diastereomer of chosen sense of P-chirality of formula III.

Figure 2:
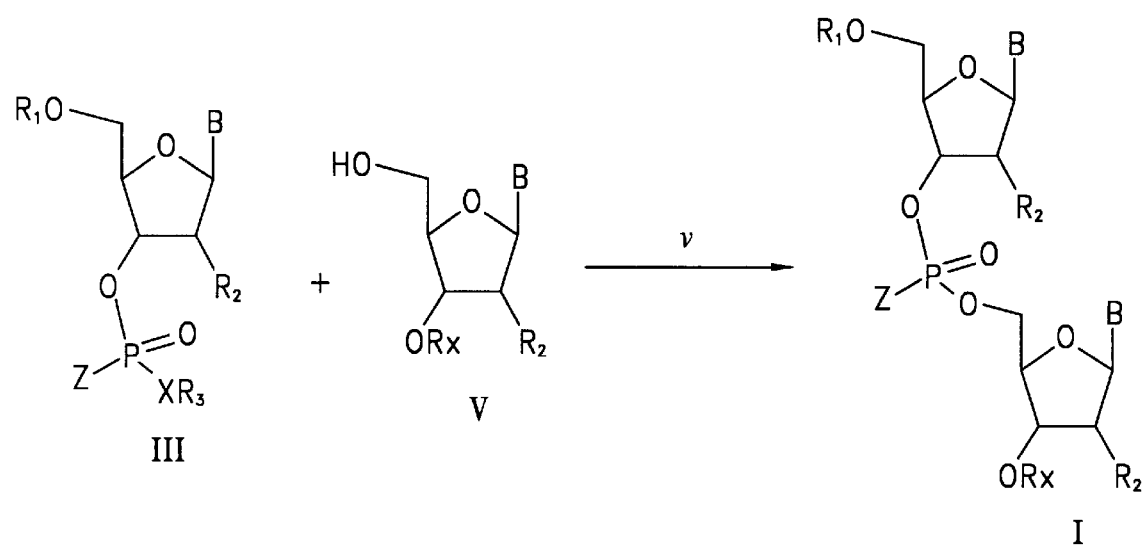
FIG. 2 depicts a synthetic scheme for coupling a chirally pure nucleoside monomer synthon of chosen sense of P-chirality to another nucleoside to give a chirally pure nucleoside dimer of chosen sense of P-chirality according to the present invention. In this figure, v) represents DBU and a lithium halide salt.

As depicted in FIG. 2, the chirally pure nucleoside monomer synthons of chosen sense of P-chirality may be conveniently coupled to a nucleoside of formula V in a stereospecific manner which conserves the chirally pure P-chiral center by coupling a compound of formula III and a compound of formula V in the presence of a lithium halide salt and an activator, preferably DBU, to give a dimer of formula I. For convenience, the reaction is carried out in an inert organic solvent. Suitable solvents include dichloromethane, benzene, pyridine, toluene, DMF, acetonitrile and other inert organic solvents.

It should be noted that according to the reaction schemes set forth in FIGS. 1 to 3, X may be either selenium or sulfur. Under certain situations use of selenium compounds may be preferred and alternatively, under other situations, sulfur compounds may be preferred. Use of the selenium compounds in the present synthetic scheme may result in shorter reaction times than when corresponding sulfur compounds are employed. However, under certain conditions, such as larger scale or industrial syntheses, use of sulfur compounds may be preferable due to environmental factors and concerns related to safety and/or toxicity of the selenium compounds and resulting side products.

B. Preferred Compounds and Intermediates
(i) Preferred Compounds of Formula I:

Preferred compounds of formula I include those compounds wherein (a) R$_1$ is a protecting group, (b) each R$_2$ is independently selected from hydrogen, optionally protected hydroxy, halogen, chloroalkyl or fluoroalkyl of 1 to 4 carbon atoms and 1 to 9 chlorine or fluorine atoms, cyano, azido, optionally protected amino, perfluoroalkyl of 1 to 4 carbon atoms, perfluoroalkoxy of 1 to 4 carbon atoms, alkoxyalkyl, vinyl, ethynyl -Q$_1$, -OQ$_1$, -SQ$_1$ or NHQ$_1$ wherein -Q$_1$ is alkyl of 1 to 12 carbon atoms, aryl of 1 to 12 carbon atoms, aralkyl of 2 to 15 carbon atoms, alkaryl of 2 to 15 carbon atoms, alkenyl of 3 to 12 carbon atoms, and alkynyl of 3 to 12 carbon atoms; (c) B is an independently selected optionally protected nucleoside base; (d) Z is independently selected from -Q$_1$, vinyl, ethynyl, optionally protected aminomethyl and optionally protected aminoethyl; and (e) R$_X$ is an aroyl protecting group, acyl protecting group, alkoxycarbonyl protecting group, benzenesulfonyl or ring-substituted benzenesulfonyl protecting group, a coupling group a, silyl protecting group, a 5'-O-nucleotide analog, a 5'-O-oligonucleotide analog or an alkyl protecting group.

Preferred compounds of formula I, as well as the nucleoside monomer synthons and intermediates of formulas II to IV, include those compounds where R$_2$ is selected from hydrogen, optionally protected hydroxy, halogen, vinyl, cyano, azido, optionally protected amino, alkoxyalkyl of 1 to 6 carbon atoms, -Q$_1$, -OQ$_1$, -SQ$_1$ and -NHQ$_1$ wherein -Q$_1$ is lower alkyl of 1 to 4 carbon atoms or alkenyl of 3 to 4 carbon atoms. Especially preferred R$_2$ groups include hydrogen, optionally protected hydroxy, methoxy, fluoro, azido, -O-allyl and optionally protected amino. Preferred compounds of formula I and nucleoside monomer synthons and intermediates of formulas II to IV include compounds wherein Z is optionally protected aminomethyl, optionally protected aminoethyl or -Q$_1$ wherein -Q$_1$ is lower alkyl of 1 to 4 carbon atoms. Especially preferred Z groups include methyl.

Suitable R$_1$ groups include protecting groups conventionally used in oligonucleotide synthesis which are removable under non-adverse conditions. These groups include groups such as triphenylmethyl protecting groups such as p-anisoyldiphenylmethyl, di(p-anisoyl) phenylmethyl (4,4'-dimethoxytrityl or "DMT") groups and other conventional protecting groups such as 9-phenylxanthene-9-ol ("Px").

Preferred R$_X$ groups include acyl protecting groups, silyl protecting groups such as t-butyldimethylsilyl, and other similar protecting groups.

(ii) Preferred Compounds of Formula II

Preferred compounds of Formula II include those compounds wherein (a) R$_1$ is a protecting group, (b) each R$_2$ is independently selected from hydrogen, optionally protected hydroxy, halogen, chloroalkyl or fluoroalkyl of 1 to 4 carbon atoms and 1 to 9 chlorine or fluorine atoms, cyano, azido, optionally protected amino, perfluoroalkyl of 1 to 4 carbon atoms, perfluoroalkoxy of 1 to 4 carbon atoms, alkoxyalkyl, vinyl, ethynyl -Q$_1$, -OQ$_1$, -SQ$_1$ or -NHQ$_1$ wherein -Q$_1$ is alkyl of 1 to 12 carbon atoms, aryl of 1 to 12 carbon atoms, aralkyl of 2 to 15 carbon atoms, alkaryl of 2 to 15 carbon atoms, alkenyl of 3 to 12 carbon atoms, and alkynyl of 3 to 12 carbon atoms; (c) B is an independently selected optionally protected nucleoside base; (d) Z is independently selected from -Q$_1$, vinyl, ethynyl, optionally protected aminomethyl and optionally protected aminoethyl; (e) X is sulfur or selenium; and (f) Ar is phenyl optionally substituted with 1 to 5 substitutients independently selected from halogen, nitro, and lower alkyl of 1 to 6 carbon atoms.

Suitable protecting groups for nucleoside bases and amino groups are known in the art.

Suitable $R_1$ groups include protecting groups conventionally used in oligonucleotide synthesis which are removable under non-adverse conditions. These groups include groups such as triphenylmethyl protecting groups such as p-anisoyldiphenylmethyl, di(p-anisoyl) phenylmethyl (4,4'-dimethoxytrityl or "DMT") groups and other conventional protecting groups such as 9-phenylxanthene-9-ol ("Px").

Novel compounds of formula II include those as set forth above with the proviso that when $R_2$ is hydrogen, then Ar is not unsubtituted phenyl. According to an alternate preferred aspect, when Ar is unsubtituted phenyl, $R_2$ is not hydrogen, hydroxyl or methoxy.

(iii) Preferred Compounds of Formula III

Preferred compounds of formula III include those compounds where (a) $R_1$ is a protecting group; (b) each $R_2$ is independently selected from hydrogen, optionally protected hydroxy, halogen, chloroalkyl or fluoroalkyl of 1 to 4 carbon atoms and 1 to 9 chlorine or fluorine atoms, cyano, azido, optionally protected amino, perfluoroalkyl of 1 to 4 carbon atoms, perfluoroalkoxy of 1 to 4 carbon atoms, alkoxyalkyl, vinyl, ethynyl $-Q_1$, $-OQ_1$, $-SQ_1$ or $-NHQ_1$ wherein $-Q_1$ is alkyl of 1 to 12 carbon atoms, aryl of 1 to 12 carbon atoms, aralkyl of 2 to 15 carbon atoms, alkaryl of 2 to 15 carbon atoms, alkenyl of 3 to 12 carbon atoms, and alkynyl of 3 to 12 carbon atoms; (c) B is an independently selected optionally protected nucleoside base; (d) Z is independently selected from $-Q_1$, vinyl, ethynyl, optionally protected aminomethyl and optionally protected aminoethyl; (e) $R_3$ is $-Q_1$; and (f) X is selenium or sulfur.

Suitable protecting groups for nucleoside bases and amino groups are known in the art.

Suitable $R_1$ groups include protecting groups conventionally used in oligonucleotide synthesis which are removable under non-adverse conditions. These groups include groups such as triphenylmethyl protecting groups such as p-anisoyldiphenylmethyl, di(p-anisoyl) phenylmethyl (4,4'-dimethoxytrityl or "DMT") groups and other conventional protecting groups such as 9-phenylxanthene-9-ol ("Px").

Novel compounds of formula III include those compounds as described above with the proviso that when $R_2$ is hydrogen, optionally protected hydroxy or methoxy, then $R_3$ is not methyl, benzyl or nitrobenzyl.

(iv) Preferred Compounds of Formula IV

Preferred compounds of formula IV include those compounds wherein (a) $R_1$ is a protecting group; (b) each $R_2$ is independently selected from hydrogen, optionally protected hydroxy, halogen, chloroalkyl or fluoroalkyl of 1 to 4 carbon atoms and 1 to 9 chlorine or fluorine atoms, cyano, azido, optionally protected amino, perfluoroalkyl of 1 to 4 carbon atoms, perfluoroalkoxy of 1 to 4 carbon atoms, alkoxyalkyl, vinyl, ethynyl $-Q_1$, $-OQ_1$, $-SQ_1$ or $-NHQ_1$ wherein $-Q_1$ is alkyl of 1 to 12 carbon atoms, aryl of 1 to 12 carbon atoms, aralkyl of 2 to 15 carbon atoms, alkaryl of 2 to 15 carbon atoms, alkenyl of 3 to 12 carbon atoms, and alkynyl of 3 to 12 carbon atoms; (c) B is an independently selected optionally protected nucleoside base; (d) Z is independently selected from $-Q_1$, vinyl, ethynyl, optionally protected aminomethyl and optionally protected aminoethyl; and (e) Ar is phenyl optionally substituted with 1 to 5 substitutients independently selected from halogen, nitro, cyano and lower alkyl of 1 to 6 carbon atoms.

Suitable protecting groups for nucleoside bases and amino groups are known in the art.

Suitable $R_1$ groups include protecting groups conventionally used in oligonucleotide synthesis which are removable under non-adverse conditions. These groups include groups such as triphenylmethyl protecting groups such as p-anisoyldiphenylmethyl, di(p-anisoyl) phenylmethyl (4,4'-dimethoxytrityl or "DMT") groups and other conventional protecting groups such as 9-phenylxanthene-9-ol ("Px").

(v) Preferred Compounds of Formula V

Preferred compounds of formula V include those compounds wherein (a) each $R_2$ is independently selected from hydrogen, optionally protected hydroxy, halogen, chloroalkyl or fluoroalkyl of 1 to 4 carbon atoms and 1 to 9 chlorine or fluorine atoms, cyano, azido, optionally protected amino, perfluoroalkyl of 1 to 4 carbon atoms, perfluoroalkoxy of 1 to 4 carbon atoms, alkoxyalkyl, vinyl, ethynyl $-Q_1$, $-OQ_1$, $-SQ_1$, or $-NHQ_1$, wherein $-Q_1$ is alkyl of 1 to 12 carbon atoms, aryl of 1 to 12 carbon atoms, aralkyl of 2 to 15 carbon atoms, alkaryl of 2 to 15 carbon atoms, alkenyl of 3 to 12 carbon atoms, and alkynyl of 3 to 12 carbon atoms; (b) B is an independently selected optionally protected nucleoside base; (c) Z is independently selected from $-Q_1$, vinyl, ethynyl, optionally protected aminomethyl and optionally protected aminoethyl; and (d) $R_X$ is an aroyl protecting group, acyl protecting group, alkoxycarbonyl protecting group, benzenesulfonyl or ring-substituted benzenesulfonyl protecting group, a coupling group, a silyl protecting group such as a t-butyltrimethylsilyl group, a 5'-O-nucleotide analog, a 5'-O-oligonucleotide analog, or an alkyl protecting group.

Suitable protecting groups for nucleoside bases and amino groups are known in the art.

Suitable $R_1$ groups include protecting groups conventionally used in oligonucleotide synthesis which are removable under non-adverse conditions. These groups include groups such as triphenylmethyl protecting groups such as p-anisoyldiphenylmethyl, di(p-anisoyl) phenylmethyl (4,4'-dimethoxytrityl or "DMT") groups and other conventional protecting groups such as 9-phenylxanthene-9-ol ("Px").

C. Use of Compounds and Oliaonucleotides

The limitations of the available methods for modification and synthesis of the organophosphorus derivatives have led to a continued need for other modifications which provide resistance to nucleases and satisfactory hybridization properties for antisense oligonucleotide diagnostics, therapeutics, and research. All references which have been cited below are hereby incorporated by reference in their entirety.

The organophosphorus derivatives of this invention can be used in preparing oligonucleotides useful for diagnostics, therapeutics, as research reagents and for use in kits.

Chirally pure organophosphorus derivatives may be used in synthesizing oligonucleosides of preselected chirality, either enriched for $R_p$ configuration, $S_p$ configuration or a mixture thereof.

In particular, organophosphorus dinucleoside derivatives of the present invention of a defined sense of chirality at the phosphorus atom of the phosphonate moiety may be coupled together using an automated DNA synthesizer. The dimer synthons have coupling groups which allow them to be coupled together to give a chirally enriched phosphonate oligomer (see Examples 5 to 13). From a stock of prepared organophosphorus dinucleoside derivatives, oligonucleotides of any nucleoside base sequence may be synthesized by linking together the appropriate dinucleotides. Dinucleotides are added to the growing oligonucleotide chain until an oligonucleotide having the desired number of nucleosides is obtained. The resulting oligonucleotide has a defined sense of the P-chirality at every other linkage.

Since the oligonucleotides thus produced may form duplexes or triple helix complexes or other forms of stable association with transcribed regions of nucleic acids, they may be used to interfere or inhibit or alter expression of a particular gene or target sequence in a living cell, allowing selective inactivation or inhibition or alteration of expression. The target sequence may be RNA, such as a pre-mRNA or an mRNA or DNA. They also may be used as diagnostic agents to detect the presence of a particular mucleic acid target sequence, either in vivo or in vitro.

Many diseases are characterized by the presence of undesired DNA or RNA, which may be in certain instances single stranded and in other instances double stranded. These diseases can be treated using the principles of antisense therapy as is generally understood in the art.

To assist in understanding the present invention, the following examples are included which describe the results of a series of experiments. The following examples relating to this invention should not, of course, be construed as specifically limiting the invention and such variation of the invention, now known or later developed, which would be within the purview of one skilled in the art are considered to fall within the scope of the invention as described herein and hereinafter claimed. Accordingly, the following examples are offered by way of illustration and not by way of limitation.

In the Examples set forth herein below, the P-chirally pure diastereomers are identified as the FAST or the SLOW isomer as determined by chromatography rather than by Rp or Sp or chosen or unchosen sense of P-chirality. When compound IIUC is converted to compound III, chirality at the phosphorus atom is retained, however a FAST IIC is converted to a SLOW III and a SLOW IIC is converted to a FAST III. When compound IIUC is converted to IV, a FAST IIUC yields a FAST IV and a SLOW IIUC yields a SLOW IV. When compound IV is converted to III, a FAST IV yields a FAST III and a SLOW IV yields a SLOW III.

When compound III is coupled to compound V according to the stereospecific coupling reaction of FIG. 2, with retention of chirality at the phosphorus atom, a FAST III yields a SLOW I and a SLOW III yields a FAST I. Also in the Examples, "a" (such as IIIa) refers to the FAST isomer of a diastereomer pair and "b" (such as IIIb) refers to the SLOW isomer of the pair. In the case of the dinucleotides, it is believed that the FAST isomer (on normal phase chromatography) corresponds to the Rp isomer.

EXAMPLES

Example 1
General Procedure for the Synthesis of a Compound of Formula II (where Z=CH$_3$, X=S and Ar=phenyl)

To a solution of methyldichlorophosphine (0.29 g, 2.5 mmol) and triethylamine (0.55 g, 5.5 mmol), in THF, cooled to −40° C., was added slowly a solution of the appropriately protected nucleoside (1.0 mmol) in THF (10 mL). After 30 minutes the reaction mixture was allowed to warm to room temperature and aniline (0.28 g, 3.0 mmol) was added dropwise, followed by elemental sulfur. The reaction was followed by tlc and when complete the reaction mixture was diluted with chloroform and extracted with aqueous NaHCO$_3$ solution. The extracts were dried over anhydrous Na$_2$SO$_4$ and concentrated under reduced pressure to provide a crude product that was purified by flash chromatography on silica gel (230–400 mesh) using a mixture of heptane (10–20%) in chloroform. Appropriate fractions were combined and concentrated under reduced pressure to yield the desired product as a mixture of diastereomers.

Example 2
Preparation of [Rp,Sp]-5'-O-DMT-Thymidine 3'-O-(Methylphosphonoanilidothioate)

The title compound mixture was prepared from 5'-O-DMT-thymidine (0.540 g, 1 mmol) following the general procedure described in Example 1 and was obtained as a solid white foam. Yield: 0.66 g (93%). $^{31}$P NMR (CDCl$_3$) δ 79.44, 79.58; MS (FAB$^-$) m/e 712.4 [(M-H)$^-$].

Example 3
Preparation of [Rp,Sr]-5'-O-DMT-N$^4$-Benzoyl-2'-Deoxycytidine 3'-O-(Methylphosphonoanilidothioate)

The title compound mixture was prepared from 5'-O-DMT-N$^4$-benzoyl-2'-deoxycytidine (1 mmol) following the general procedure described in Example 1 and was obtained as a colorless foam. Yield: 70%. $^{31}$P NMR (CDCl$_3$/C$_6$D$_6$) δ 79.38, 79.74.

Example 4
Preparation of [Rp,Sp]-5'-O-DMT-N$^6$-Benzoyl-2'-Deoxyadenosine 3'-O-(Methylphosphonoanilidothioate)

The title compound mixture was prepared from 5'-O-DMT-N$^6$-benzoyl-2'-deoxyadenosine (0.657 g, 1 mmol) following the general procedure described in Example 1 and was obtained as a colorless foam. Yield: 75%. $^{31}$P NMR (CDCl$_3$) δ 79.21, 79.60.

Example 5
Preparation of [Rp,Sp]-5'-O-DMT-N$^2$-Isobutyryl-2'-Deoxyguanosine 3'-O-(Methylphonoanilidothioate)

The title compound mixture was prepared from 5'-O-DMT-N$^2$-Isobutyryl-2'-deoxyguanosine (0.640 g, 1 mmol) following the general procedure described in Example 1 and was obtained as a white foam. Yield: 0.71 g (98%). $^{31}$P NMR δ (CDCL$_3$): 79.65, 79.72.

Example 6
Preparation of [Rp,Sp]-5'-O-DMT-2'-O-Methyl Uridine 3'-O-(Methylphosphonoanilidothioate)

The title compound mixture was prepared from 5'-O-DMT-2'-O-Methyl uridine (0.560 g, 1 mmol) following the general procedure described in Example 1 and was obtained as a colorless foam. Yield: 0.68 g (85%). $^{31}$P NMR δ (CDCl$_3$): 81.96, 81.38.

Example 7
Preparation of [Rp,Sp]-5'-O-DMT-2'-O-Methyl-Uridine 3'-O-(Methylphosphonoanilidothioate)

The title compound was prepared from 5'-O-DMT-2'-O-methyl-uridine (0.560 g, 1 mmol), following general procedure described in Example 1 and was obtained as white powder after precipitation from hexane. Yield: 0.58 g (80%). $^{31}$P NMR δ (CDCl$_3$): 81.33, 81.96. FAB$^-$MS [M-H]: 728.3.

Example 8
Preparation of [Rp,Sp]-5'-O-DMT-N$^4$-Isobutyryl-2'-O-Methyl-cytidine 3'O-(Methylphosphonoanilidothioate)

The title compound was prepared from 5'-O-DMT-N$^4$-isobutyryl-2'-O-methyl-cytidine (0.63 g, 1 mmol) following the general procedure described in Example 1 and was obtained as a white powder after precipitation from petroleum ether. Yield: 0.56 g (71%). $^{31}$P NMR δ (CDCl$_3$): 79.49, 81.65. FAB$^-$MS [M-H]: 797.4.

Example 9
Preparation of [Rp,Sp]-5'-O-DMT-N$^6$-Benzoyl-2'-O-Methyl-adenosine-3'-O-(Methylphosphonoanilidothioate)

The title compound was prepared from 5'-O-DMT-N$^6$-benzoyl-2'-O-methyl-adenosine (0.69 g, 1 mmol) following the general procedure described in Example 1 and was obtained as a white foam. Yield: 0.64 g (75%). $^{31}$P NMR δ (CDCl$_3$): 81.38, 81.43 m. FAB$^-$MS[M-1]: 855.4.

Example 10
Preparation of [Rp,Sp]-5'-O-DMT-N$^2$-Isobutyryl-2'-O-Methyl-guanosine 3'-O-(Methylphosphonoanilidothioate)

The title compound was prepared from 5'-O-DMT-N$^2$-isobutyryl-2'-O-methyl-guanosine (0.67 g, 1 mmol) following the general procedure described in Example 1 and was obtained as a white foam. Yield: 0.45 g (54%). $^{31}$P NMR δ (CDCl$_3$): 81.16, 81.88. FAB$^-$MS[M-1]: 836.4.

Example 11
Separation of Diastereomers of Formula II

Separation of the Rp and Sp diastereomers of Formula II described in Examples 2 through 6 was carried out by flash chromatography on silica gel using a mixture of 10 to 20% heptane in chloroform as eluent.

For convenience of reference, the FAST, isomer will be referred to with an "a" after the compound number, such as compound "IIa" and the SLOW isomer will be referred to with a "b" after the compound number, such as compound "IIb".

TABLE 1

| Example/Base | Diastereomer* | $^{31}$P NMR (δ) |
|---|---|---|
| 2; B = Thymine | FAST | 79.44 |
|  | SLOW | 79.58 |
| 3; B = Cytosine | FAST | 79.38 |
|  | SLOW | 79.74 |
| 4; B = Adenine | FAST | 79.21 |
|  | SLOW | 79.60 |
| 5; B = Guanine | FAST | 79.65 |
|  | SLOW | 79.72 |
| 6; B = Uracil | FAST | 81.38 |
|  | SLOW | 81.96 |

*Determined by mobility on Silica gel (Kieselgel 60, 240–400 mesh); eluent CHCl$_3$/MeOH (95:5 v/v)

Example 12
General Procedure for the Synthesis of 5'-O-DMT-(N-Protected) Nucleoside 3'-O-(S-Q$_1$-Substituted-Methylphosphonothioates) (Formula III, Z=CH$_3$, and R$_3$=Benzyl)

To a stirred solution of the corresponding nucleoside 3'-O-(methylphosphonoanilidothioate) (II) (1 mmol), in dry DMF (10 mL) was added NaH (1.2 molar equivalents) in several portions. Stirring was continued until evolution of hydrogen had ceased. To the resulting slurry was introduced a stream of dry gaseous CO$_2$. The reaction progress was monitored by TLC. Alkylating agent, Q$_1$-halide (5 mmol), was added to the reaction mixture. When the reaction was complete, solvents and excess Q$_1$-halide were removed by rotary evaporation. The solid residue was dissolved in CHCl$_3$ and washed with saturated aqueous NaHCO$_3$ solution, dried and concentrated. The crude product was purified by flash chromatography on silica gel using 0 to 5% ethanol in chloroform as eluent. When compound II was reacted as a mixture of diastereomers, the purification process was combined with the separation process to provide pure diastereomers of IIIb (SLOW), and IIIa (FAST).

Example 13
Preparation of 5'-O-DMT-Thymidine 3'-O-(S-Benzyl Methylphosphonothioate)

The title compound was prepared from the corresponding compound of formula II (B=Thymine, Z=CH$_3$) (0.712 g, 1 mmol) following the general procedure described in Example 12. Yield: 0.55 g (86%). $^{31}$P NMR δ (CDCl$_3$): 56.44, 55.94.

Example 14
Preparation of 5'-O-DMT-N$^4$-Benzoyl-2'-Deoxycytidine 3'-O-(S-Benzyl Methylphosphonothioate)

The title compound was prepared from the corresponding compound of formula II (B=Cytosine, Z=CH$_3$) (1 mmol), following the general procedures described in Example 12. Yield: 82%. $^{31}$P NMR δ (CDCl$_3$): 55.41, 55.21.

Example 15
Preparation of 5'-O-DMT-N$^6$-Benzoyl-2'-Deoxyadenosine 3'-O-(S-Benzyl Methylphosphonothioate)

The title compound was prepared from the corresponding compound of formula II (B=Adenine, Z=CH$_3$) (1 mmol), following the general procedure described in Example 12. Yield: 75%. $^{31}$P NMR δ (CH$_2$Cl$_2$/C$_6$D$_6$): 55.80, 55.21 ppm.

Example 16
Preparation of 5'-O-DMT-N$^4$-Isobutyryl-2'-Deoxyguanosine 3'-O-(S-Benzyl Methylphosphonothioate)

The title compound was prepared from the corresponding compound of formula II (B=guanine, Z=CH$_3$) (1 mmol) following the general procedure described in Example 12. Yield: 75%. $^{31}$P NMR δ (CDCl$_3$): 56.01, 55.85.

Example 17
Preparation of SLOW-5'-O-DMT-2'-O-Methyl-Uridine 3'-O-(S-Methyl Methyliphosphonothioate)

The title compound was prepared from the corresponding FAST isomer of formula IIa (B=Uracyl, Z=CH$_3$, R$_2$=O-Methyl) following the general procedure described in Example 12. Yield: 65%. $^{31}$P NMR δ (CDCl$_3$): 56.58. FAB$^-$MS[M-H]: 667.3.

Example 18
Preparation of SLOW-5'-O-DMT-2'-deoxythymidine 3'-O-(S-Methyl Methyliphosphonothioate)

The title compound was prepared from the corresponding FAST isomer of formula IIa (B=Thymine, Z=CH$_3$, R$_2$=H) following the general procedure described in Example 12. Yield: 80%. $^{31}$P NMR δ (CDCl$_3$): 55.45. FAB$^-$MS[M-H]: 652.3.

Example 19
Preparation of SLOW-5'-O-DMT-N$^4$-Isobutyryl-2'-O-Methyl-cytidine 3'-O-(S Methyl Methylphosphonothioate)

The title compound was prepared from the corresponding FAST isomer of formula IIa (B=Cytosine, Z=CH$_3$, R$_2$=O-Methyl) following the general procedure described in Example 12. Yield: 65%. $^{31}$P NMR δ (CDCl$_3$): 58.95d. FAB-MS[M-H]: 736.4.

Example 20
Preparation of SLOW-5'-O-DMT-N$^4$-Isobutyryl-2'-deoxycytidine 3'-O-(S Methyl Methylphosphonothioate)

The title compound was prepared from the corresponding FAST isomer of formula II (B=Cytosine, Z=CH$_3$, R$_2$=H) following the general procedure described in Example 12. Yield: 75%. $^{31}$P NMR δ (CDCl$_3$): 56.85. FAB-MS[M-H]: 706.4.

Example 21
Preparation of SLOW-5'-O-DMT-N$^6$-Benzoyl-2'-O-Methyl-adenosine3'-O-(S-Methyl Methylphosphonothioate)

The title compound was prepared from the corresponding FAST isomer of formula IIa (B=Adenine, Z=CH$_3$, R$_2$=O-Methyl) following the general procedure described in Example 12. Yield: 63%. $^{31}$P NMR δ (CDCl$_3$): 57.12. FAB$^-$MS (M-H): 794.4.

Example 22
Preparation of SLOW-5'-O-DMT-N$^4$-Isobutyryl-2'-O-Methyl-auanosine 3'-O-(S-Methyl Methylphosphonothioate)

The title compound was prepared from the corresponding compound of formula II (B=Guanine, Z=CH$_3$, R$_2$=O-Methyl) following the general procedure described in Example 12. Yield: 64%. $^{31}$P NMR δ (CDCl$_3$): 58.09. FAB-MS [M-H]: 775.3.

Example 23
Oxidation of (FAST) 5'-O-DMT-Thymidine 3'-O-(Methylphosphonothioanilidate) IIa to (FAST) 5'-O-DMT-Thymidine 3'-O-(Methylphosphonoanilidate) IVa Using Potasium Peroxymonosulfate To a solution of compound IIa (FAST) (0.072 g, 1 mmol) in a mixture of MeOH and THF was added an aqueous solution of Potasium Peroxymonosulfate (pH 6.7 to 7, 2 mmols). After 10 minutes a solution of 10% aqueous Na$_2$S$_2$O$_3$ was added and the mixture was extracted with chloroform. The extracts were dried over anhydrous Na$_2$SO$_4$ and concentrated. The crude product was purified by flash chromatography on silica gel using a mixture of 10 to 20% heptane in chloroform as eluent to afford 0.047 g (73%) of diastereomerically pure (FAST)-IVa. $^{31}$P NMR δ (CDCl$_3$): 30.1. MS (FAB-) m/e 696.4 [(M-H)$^-$].

Example 24
Oxidation of (SLOW) 5'-O-DMT-Thymidine 3'-O-(Methylphosphonothioanilidate) compound IIb to (SLOW) 5'-O-DMT-Thymidine 3'-O-(Methylphosphonoanilidate) IVb Using Potasium Peroxymonosulfate Conversion of compound IIb (SLOW) to IVb (SLOW) was carried out using procedures analogous to those described in Example 23. Yield: 70%. $^{31}$P NMR (CDCl$_3$) δ 29.89.

Example 25
Conversion of 5'-O-DMT-Thymidine 3'-O-Methanephosphonoanilidate IV to 5'-O-DMT-Thymidine 3'-O-(S-Benzyl Methylphosphonothioate) III Compound IV (FAST or SLOW isomer) was dried prior to reaction and then dissolved in THF (2 mL). To this solution was added 1,8-diazabicyclo[5.4.0]undec-7-ene (DBU) (0.02 mL) and the reaction mixture was stirred at ambient temperature for 45 minutes, followed by addition of CS$_2$ (1 mL). After 20 minutes benzyl bromide was added (5 equivalents) and the reaction progress was monitored by tlc. When the reaction was complete the mixture was diluted with water and extracted with chloroform. The extracts were dried over anhydrous Na$_2$SO$_4$ and concentrated. The crude product was purified by flash chromatography on silica gel using 0–5% ethanol in chloroform as eluent.

From compound IVa (FAST), product IIIa (FAST) was obtained in 65% yield. $^{31}$P NMR δ (CDCl$_3$): 56.85. Compound IVb (SLOW) was converted to IIIb (SLOW) in 70% yield. $^{31}$P NMR δ (CDCl$_3$): 55.38.

Example 26
General Procedure for the Synthesis of Dinucleoside(3',5') Methylphosphonates (FAST)-Ia or (SLOW)-Ib (Z=CH$_3$)

The corresponding diastereomerically pure compounds of formula III (SLOW or FAST) (0.3 mmol) and 3'-O-acetyl (N-protected)-2'-deoxynucleoside (compound V) (0.1 mmol) were dried prior to reaction and then dissolved in dry pyridine (5 mL). To this solution was added lithium chloride (0.125 g, 3 mmol), followed by a solution of DBU (0.456 g, 3 mmol) in pyridine (1.5 mL) in one portion. The reaction was stirred at room temperature and its progress was monitored by tlc. After the reaction was complete, solvent was evaporated and the oily residue was dissolved in chloroform and extracted with phosphate buffer. The organic extracts were dried over anhydrous Na$_2$SO$_4$ and concentrated. The crude product was purified by flash chromatography on silica gel using a mixture of 0 to 3% ethanol in chloroform as eluent.

Example 27
Preparation of (FAST)-5'-O-DMT-Thymidylyl-(3',5')-3'-O-Acetylthymidine 3'-Methylphosphonate The title compound was prepared from the corresponding compound (SLOW)-IIIb following the general procedure described in Example 26. Yield: 85%. $^{31}$P NMR δ (CDCl$_3$): 33.00. $^1$H NMR δ (CDCl$_3$): 1.58 (d, 3H, P-CH$_3$); J$_{P-H}$=17.64 Hz. MS (FAB$^-$) m/e 887 [(M-H)$^-$].

Example 28
Preparation of (FAST)-N$^4$Benzoyl-5'-O-DMT-2'-Deoxycytidylyl-(3',5')-N$^4$-Benzoyl-3'-O-Acetyl-2'-Deoxycytidine 3'-Methylphosphonate The title compound was prepared from the corresponding compound (SLOW)-IIIb following the general procedure described in Example 26. Yield: 73%. $^{31}$P NMR δ (CDCl$_3$): 33.08. $^1$H NMR δ (CDCl$_3$): 1.6 (d, 3H, P-CH$_3$); J$_{P-H}$=17.5 Hz. MS (FAB$^-$) m/e 1067 [(M-H)$^-$].

Example 29
Preparation of [Rp]-N$^6$-Benzoyl-5'-O-DMT-2'-deoxyadenoylyl-(3,5')-N$^6$-benzoyl-3'-O-acetyl-2'deoxyadenosine 3'-Methylphosphonate The title compound was prepared from the corresponding compound of formula (SLOW) IIIb (B=Adenine, Z=CH$_c$, R$_2$=H, XR$_3$=SMe) following the general procedure described in Example 26. Yield 40%. $^{31}$P NMR δ (CDCl$_3$): 32.57. $^1$H NMR δ (CDCl$_3$): 1.63 (3H, d, P-CH$_3$); $^2$J$_{P-H}$=17.61 Hz. FAB-MS [M-H]: 1185.8.

Example 30
Preparation of [Rp]-N$^4$-Isobutyrl-5;2'-O-deoxyguanosylyl-(3',5')-N$^4$-isobutyryl-3'-O-acetyl-2'-O-deoxyguanosine 3'-Methylphosphonate The title compound was prepared from the corresponding compound of formula (SLOW) IIIb (B-Guanine, Z-CH$_3$, R$_2$=H, XR$_3$=SBz) following the general procedure described in Example 26. Yield 65%. $^{31}$P NMR δ (CDCl$_3$): 33.13. $^1$H NMR δ (CDCl$_3$): 1.65 (3H, d, P-CH$_3$); $^2$J$_{P-H}$=17.59 Hz. FAB-MS [M-H]: 1077.4.

Example 31
Preparation of [Rp]-5'-O-DMT-2'-O-Methyl-Uridylyl-(3',5')-3'-O-TBDPS-2'-O-Methyl-uridine 3'-Methylphosphonate The title compound was prepared from the corresponding compound of formula (SLOW) IIIb (B=Uracyl, Z=CH$_3$, R$_2$=O-Methyl, XR$_3$=S-Methyl) following the general procedure described in Example 26. Yield: 65%. $^{31}$P NMR δ (CDCl$_3$): 33.21. $^1$H NMR δ (CDCl$_3$): 1.68 (3H, d, P-CH$_3$); $^2$J$_{P-H}$=17.5 Hz. FAB-MS [M-1]: 1115.5.

Example 32
Preparation of [Rp]-N$^6$-Isobutyryl-5'-O-DMT-2'-O-Methyl-cytidylyl-(3',5')-N$^6$-isobutyryl-3'-O-TBDPS-2'-O-Methyl-cytidine 3'-Methyliphosphonate The title compound was prepared from the corresponding compound of formula (SLOW) IIIb (B=Cytidine, Z=CH$_3$, R$_2$=O-Methyl, XR$_3$=S-Methyl) following the general procedure described in Example 26. Yield: 55%. $^{31}$P NMR δ (CDCl$_3$): 33.00. $^1$H NMR δ (CDCl$_3$): 1.65 (3H, d, P-CH$_3$). FAB-MS [M-1]: 1260.

Example 33
Preparation of [Rp]-N$^6$-Benzoyl-5'-O-DMT-2'-O-Methyl-adenoylyl-(3',5')-N$^6$-benzoyl-3'-O-TBDPS-2'-O-Methyl-adenosine 3'-Methylphosphonate The title compound was prepared from the corresponding compound of formula (SLOW) IIIb (B=Adenine, Z=CH$_3$, R$_2$=O-Methyl, XR$_3$=S-Methyl) following the general procedure described in Example 26. Yield: 68%. $^{31}$P NMR δ (CDCl$_3$): 32.9. $^1$H NMR δ (CDCl$_3$): 1.69 (3H, d, P-CH$_3$); $^2$J$_{P\text{-}H}$=17 Hz. FAB-MS [M-1]: 1307.

Example 34
Preparation of [Rp]-N$^4$-Isobutyryl-5'-O-DMT-2'-O-Methyl-guanosylyl-(3',5')-N$^4$-isobutyryl-3'-O-TBDMS-2'-O-Methyl-guanosine 3'-Methylphosphonate The title compound was prepared from the corresponding compound of the formula (SLOW) IIIb (B=Guanine, Z=CH$_3$, R$_2$=O-Methyl, XR$_3$=S-Methyl) following the general procedure described in Example 26. Yield: 45%. $^{31}$P NMR δ (CDCl$_3$): 33.14 ppm. $^1$H NMR δ (CDCl$_3$): 1.68 (3H, d, P-CH$_3$). FAB-MS [M-1]: 1210.

Example 35
General Procedure for Preparation of 5'-O-DMT-(N-Protected) Nucleoside 3'-O-(Methanephosphonoanilidoselenoate) (Compound II Where Z=CH$_3$, X=Se, Ar=phenyl)

Into the solution of methyldichlorophosphine (0.23 g, 2 mmol) in THF (10 mL) and triethylamine (0.40 g, 4 mmol) cooled to −40° C. by external cooling (dry ice-acetone) was added dropwise, with magnetic stirring, a solution of corresponding 5'-O-DMT-(N-protected, except thymine) nucleoside (1 mmol) in THF (10 mL). After removal of external cooling, stirring was continued until reaction mixture reached an ambient temperature. Then, aniline (0.28 g, 3 mmol)together with elemental selenium (0.2 g, 2.5 mmol) were added in one portion. Stirring was continued overnight. An excess of selenium was removed by filtration and solvents were partially evaporated reducing the volume of reaction mixture to about 5 mL. The residue was diluted with chloroform and resulting solution was washed with saturated aqueous NaHCO$_3$. The organic fraction was dried over anhydrous MgSO$_4$ and concentrated. Product was isolated by silica gel chromatography (elution with gradient of EtOH in CHCl$_3$). Appropriate fractions were combined and concentrated under reduced pressure to give the product as a diastereomeric mixture.

Example 36
Preparation of [Rp,Sp]-5'-O-DMT-Thymidine-3'-O-(Methanephosphonoanilidoselenoate)

The title compound was prepared from 5'-O-DMT-Thymidine (0.540 g, 1 mmol) following the general procedure described in Example 35 and was obtained as a colorless foam. Yield: 0.61 g (80%). $^{31}$P NMR δ (CDCl$_3$): 76.57, 76.36; J$_{P\text{-}Se}$: 812, 814, Hz. FAB-MS [M-H]: 758, 760, 761.

Example 37
Preparation of [Rp,Sp]-5'-O-DMT-N$^6$-Benzoyl-2'-Deoxyadenosine-3'-O-(Methanephosphono-anilidoselenoate)

The title compound was prepared from 5'-O-DMT-N$^6$-benzoyl-2'-deoxyadenosine (0.633 g, 1 mmol), following the general procedure described in Example 35. A mixture of diastereomers were obtained as a colorless foam. Yield: 0.6 g (71%). $^{31}$P NMR δ (CDCl$_3$): 76.85, 76.29; J$_{P\text{-}Se}$=820 Hz. FAB-MS [M-H]: 847, 849, 850.

Example 38
Preparation of [Rp,Sp]-5'-O-DMT-N$^6$-Benzoyl-2'-O-deoxyadenosine-3'-O-(Methanephosphonoanilidoselenoate)

The title compound was prepared from the corresponding 5'-O-DMT-N$^6$-Benzoyl-2'-deoxyadenosine (0.657 g, 1 mmol) following the general procedure described in Example 35 and was obtained as a mixture of diastereomers as a colorless foam. Yield: 0.620 g (75%). $^{31}$P NMR δ (CDCl$_3$) δ: 76.56, 76.39; J$_{P\text{-}Se}$: 828 Hz. FAB$^-$MS [M-H]: 825, 827, 828.

Example 39
Preparation of [Rp,Sp]-5'-O-DMT-N$^2$-Isobutyryl-2'-O-deoxyguanosine 3'-O-(Methanephosphonoanilidoselenoate)

The title compound was prepared from the corresponding 5'-O-DMT-N$^2$-isobutyryl-2'-deoxyguanosine (0.640 g, 1 mmol) following the general procedure described in Example 35 and was obtained as a mixture of diasteromers as a colorless foam. Yield: 0.595 g (70%). $^{31}$P NMR δ (CDCl$_3$); 76.62, 76.37; J$_{P\text{-}Se}$: 823, 825 Hz. FAB$^-$MS [M-H]: 853, 855, 856.

Example 40
Conversion of SLOW-5'-O-DMT-nucleoside 3'-O-Methylphosphonothioanilidate into SLOW-5'-O-DMT-nucleoside-3'-O-Methanephosphonoanilidates by means of OXONE Substrate IIb (X-S, SLOW, 1 mmol) was dissolved in MeOH (6 mL) and THF (4 mL) and buffered (0.1M) solution of Oxone (pH −6.8 to −7.2) (2 mL) was added to the reaction mixture.

The oxidation was usually completed within 15 minutes (TLC control). The reaction was quenched by addition of 10% Na$_2$S$_2$O$_3$ and the extraction of product with CHCl$_3$ (3 to 4 times). Combined organic layers were dried over MgSO$_4$ and product IVb (X=O, SLOW) was purified by a silica gel column chromatography [CHCl$_3$ (0.1% Et$_3$N)-(0–4%) EtOH; Kieselgel 60, 230–400 mesh, Merck].

Using the same procedure, FAST compounds IIa (X=S) were converted to FAST-IVa (X=O).

Example 41
Preparation of SLOW-5'-O-DMT-Thymidine 3'-O-Methanephosphonoanilidate (X=O)

The title compound was prepared using SLOW-IIb (B=Thymine, X=S, R$_2$=H) according to general procedure described in Example 40. Yield: 91%. $^{31}$P NMR δ (CDCl$_3$): 28.78. FAB$^-$MS [M-H]: 796.4.

Example 42
Preparation of SLOW-5'-O-DMT-N$^4$-Benzoyl-2'-deoxycytidine 3'-O-Methanephosphonoanilidate (X=O)

The title compound was prepared using SLOW-IIb (B=Cytosine, X=S, R$_2$=H) according to general procedure described in Example 40. Yield: 85%. $^{31}$P NMR δ (CDCl$_3$): 29.52. FAB$^-$MS [M-H]: 865.3.

Example 43
Preparation of SLOW-5'-O-DMT-$N^6$-Benzoyl-2'-deoxyadenosine 3'-O-Methanephosphonoanilidate (X=O)

The title compound was prepared using SLOW-IIb (B=Adenine, X=S, $R_2$=H) according to general procedure described in Example 40. Yield: 80%. $^{31}$P NMR δ (CDCl$_3$): 29.85. FAB$^-$MS [M-H]: 808.3.

Example 44
Preparation of SLOW-5'-O-DMT-$N^2$-Isobutyryl-2'-deoxyguanosine 3'-O-Methanephosphonoanilidate (X=O)

The title compound was prepared using SLOW-IIb (B=Guanine, X=S, $R_2$=H) according to general procedure described in Example 40. Yield: 75%. $^{31}$P NMR δ (CDCl$_3$): 30.63. FAB$^-$MS [M-H]: 790.4.

Example 45
Preparation of SLOW-5'-O-DMT-2'-O-Methyl-Uridine 3'-O-Methanephosphonoanilidate (X=O)

The title compound was prepared using SLOW-II (B=Uracil, X=S, $R_2$=O-methyl) according to general procedure described in Example 40. Yield: 90%. $^{31}$P NMR δ (CDCl$_3$): 31.58. FAB$^-$MS [M-H]: 712.3.

Example 46
Preparation of SLOW-5'-O-DMT-$N^4$-Isobutyryl-2'-O-Methyl-cytidine 3'-O-Methanephosphonoanilidate (X=O)

The title compound was prepared using SLOW-IIb (B=Cytosine, X=S, $R_2$=O-methyl) according to general procedure described in Example 40. Yield: 75%. $^{31}$P NMR δ (CDCl$_3$): 31.07. FAB$^-$MS [M-H]: 781.4.

Example 47
Preparation of SLOW-5'-O-DMT-$N^6$-Benzoyl-2'-O-Methyl-adenosine 3'-O-Methanephosphonoanilidate (X=O)

The title compound was prepared using SLOW-IIb (B=Adenine, X=S, $R_2$=O-methyl) according to general procedure described in Example 40. Yield: 81%. $^{31}$P NMR δ (CDCl$_3$): 29.96. FAB$^-$MS [M-H]: 838.3.

Example 48
Preparation of SLOW-5'-O-DMT-$N^2$-Isobutyryl-2'-O-Methyl-guanosine 3'-O-Methanephosphonoanilidate (X=O)

The title compound was prepared using SLOW-IIb (B=Guanine, X=S, $R_2$=O-methyl) according to general procedure described in Example 40. Yield: 80%. $^{31}$P NMR δ (CDCl$_3$): 30.97. FAB-MS [M-H]: 821.3.

Example 49
General Procedure for the Preparation of Dinucleoside (3',5')-Methanephosphonates Diastereomerically pure compound III (either FAST or SLOW) (0.3 mmol) and 3'-O-acetyl (N-protected)-2'-deoxynucleoside V (0.1 mmol) were coevaporated twice with dry pyridine (5 ml) and left to stand overnight under high vacuum. Lithium chloride (freshly dried at 150° C./0.1 mm Hg, 0.125 g, 3 mmol) was added and the resulting mixture was dissolved in dry pyridine (5 ml). To this solution, DBU (0.456 g, 3 mmol) in pyridine (1.5 ml) was added in one portion. After the reaction was complete (disappearance of starting material compound III was followed by HPTLC), solvent was evaporated and the oily residue was added to cold hexane. The solid precipate was collected by centrifugation, and redissolved in CHCl$_3$. The resulting solution was extracted twice with aqueous phosphate buffer (pH=7.0). The combined organic layers were dried over anhydrous MgSO$_4$, concentrated to give crude product which was purified by column chromatography. The appropriate fractions, eluted with a CHCl$_3$-Ethanol gradient (3 to 10% ethanol), were collected, combined and concentrated under reduced pressure.

Example 50
Preparation of [Rp]-5'-O-DMT-Thymidyl-(3',5')-3'-O-acetyl thymidine 3'-Methylphosphonate The above identified dinucleotide was prepared using the corresponding [Sp]selenoate of formula III and compound of formula V and following the procedure described in Example 49. Yield: 92%. $^{31}$P NMR δ (CDCl$_3$): 33.00. $^1$H NMR δ (CDCl$_3$): 1.58 (3H, d, P-CH$_3$); J=17.64 Hz. FAB-MS [M-H]: 887.

Example 51
Preparation of [Sp]-5'-O-DMT-Thymidyl-(3',5')-O-acetyl Thymidine 3'-Methylphosphonate The above-identified nucleotide was prepared using the corresponding [Rp]-selenoate of formula III, and the corresponding compound of formula V, and following the procedures described in Example 49. Yield: 86%. $^{31}$P NMP δ (CDCl$_3$): 34.14. $^1$H NMR δ (CDCl$_3$):1.57 (3H, d, P-CH$_3$); $^2J_{P-H}$=17.59 Hz. FAB-MS [M-H]: 887.

Example 52
Preparation of [Rp]-$N^4$-Benzoyl-5'-O-DMT-2'-deoxycytidyl-(3',5')-$N^4$-Benzoyl-3'-O-acetyl-2'-deoxycytidine 3'-Methylphoshonate The above-identified dinucleotide was prepared using the corresponding SLOW [Sp]-selenoate of formula III and the corresponding compound of formula V and following the procedures described in Example 49. Yield: 80%. $^{37}$P NMR δ (CDCl$_3$): 32.98. $^1$H NMR δ (CDCl$_3$): 1.605 (3H, d, P-CH$_3$); $^2J_{P-H}$=17.55 Hz. FAB-MS [M-H]: 1067.

Example 53
Preparation of [Sp]-$N^4$-Benzoyl-5'-O-DMT-2'-deoxycytidyl-(3',5')-$N^4$-Benzoyl-3'-O-acetyl-2'-deoxycytidine 3'-Methylphosphonate The above-identified dinucleotide was prepared using the corresponding [Rp]-selenoate of formula III (0.1 mmol) and the compound of formula V (0.03 mmol) and following the procedure described in Example 49. Yield: 60%. $^{31}$P NMR δ (CDCl$_3$): 33.06. $^1$H NMR δ (CDCl$_3$): 1.66 (3H, d, P-CH$_3$); $^2J_{P-H}$=17.55 HZ. FAB-MS [M-H]: 1067.

Example 54
Preparation of [Rp]-$N^6$-Benzoyl-5'-O-DMT-2'-deoxycytidyl-(3',5')-$N^4$-Benzoyl-3'-O-acetyl-2'-deoxycytidine 3'-Methylphosphonate The above-identified dinucleotide was prepared using the corresponding [Sp]-selenoate of formula III (0.1 mmol) and the corresponding compound of formula V and following the procedures described in Example 49. Yield: 40%. $^{31}$P NMR δ (CDCl$_3$): 32.57. $^1$H NMR δ (CDCl$_3$): 1.63 C3H, d, P-CH$_3$); $^2J_{P-H}$=17.61 HZ. FAB-MS [M-H]: 1014.

Example 55
Preparation of [Sp]-$N^6$-Benzoyl-5'-O-DMT-2'-deoxyadenyl-(3',5')-$N^6$-Benzoyl-3'-O-acetyl-2'-deoxyadenosine 3'-Methylphosphonate The above-identified dinucleotide was prepared using the corresponding [Rp]-selenoate of formula III (0.1 mmol) and the corresponding compound of formula V (0.4 mmol). Yield: 45%. $^{31}$P NMR δ (CDCl$_3$):32.71. $^1$H NMR δ (CDCl$_3$): 1.60 (3H, d, P-CH$_3$); $^2J_{P-H}$=17.54 ppm. FAB-MS [M-H]: 1014.

Example 56
Preparation of [R$_p$]-N$^4$-Isobutyryl-5'-O-DMT-2'-deoxyguanylyl-(3',5')-N$^4$-isobutyryl-3'-O-acetyl-2'-deoxyguanosine 3'-Methylphosphonate The above-identified dinucleotide was prepared using the corresponding [Sp]-selenoate of formula II and the corresponding compound of formula V and following the procedures described in Example 49. Yield: 65%. $^{31}$P NMP δ (CDCl$_3$)δ: 33.13. $^1$H NMR δ (CDCl$_3$): 1.65 (3H, d, P-Ch$_3$); $^2$J$_{P-H}$=17.59 Hz. FAB$^-$MS [M-H]: 1073.

Example 57
Preparation of [Sp]-N$^4$-Isobutyryl-5'-O-DMT-2'-deoxyguanylyl-(3',5')-N$^4$-isobutyryl-3'-O-acetyl-2'-deoxyguanosine 3'-Methylphosphonate The above-identified dinucleotide was prepared using the corresponding [Rp]-selenoate of formula III (0.2 mmol) and the corresponding compound of formula V (0.08 mmol) and following the procedures described in Example 49. Yield: 30% (not optimized). $^{31}$P NMR δ (CDCl$_3$): 33.33. $^1$H NMR δ (CDCl$_3$): 1.65 (3H, d,P-CH$_3$); $^2$J$_{P-H}$=17.4 Hz. FAB$^-$MS [M-H]: 983, 984.

Example 58
Preparation of [Rp]-5'-O-DMT-Thymidyl-(3',5')-N$^4$-isobytyryl-3'-O-acetyl-2'-deoxyguanosine 3'-Methylphosphonate The above-identified dinucleotide was prepared using the corresponding [Sp]-5'-O-DMT-Thymidine 3'-O(Se Methyl Methanephosphoroselenolate) of formula III (0.25 mmol) and the corresponding N$^4$-isobutyryl 3'-O-acetyl-2'-deoxyguanosine of formula V (0.1 mmol) and following the procedures described in Example 49. Yield: 70%. $^{31}$P NMR δ (CDCl$_3$): 33.33. $^1$H NMR δ (CDCl$_3$): 1.55 (3H, d, P-CH$_3$); $^2$J$_{P-H}$=17.57 Hz. FAB$^-$MS [M-H]: 983, 984.

Example 59
Preparation of [Sp]-5'-P-DMT-Thymidiyly-(3;5')-N$^4$-isobutyryl-3'-O-acetyl-2-deoxyguanosine 3'-Methylphosphonate The above-identified dinucleotide was prepared using the corresponding [Rp]5'-O-DMT-Thymidine-3'-O-(Se-methyl methanephosphonoselenolate) of formula III (0.25 mmol) and the corresponding N$^4$-isobutyryl-3'-O-acetyl-2'-deoxyguanosine of formula V (0.1 mmol) and following the procedures described in Example 49. Yield: 93%. $^{31}$P NMR δ (CDCl$_3$): 33.17. $^1$H NMR δ (CDCl$_3$): 1.63 (3H, d, P-CH$_3$); $^2$J$_{P-H}$=17.61 Hz. FAB-MS [M-H]: 983, 984, 985.

Example 60
General Procedure for Preparation of Fully Protected Trimers, Tetramers and Pentamers A. Removal of 5'-O-DMT Group The fully protected dinucleotide (for preparation of a trimer), trimer (for preparation of a tetramer) or tetramer (for preparation of a pentamer) was dissolved in 3% trichloroacetic acid in dichloromethane and stirred at room temperature. After 10 minutes, the reaction was quenched with a saturated solution of aqueous NaHCO$_3$, and then extracted with the same buffer solution. Combined organic layers were concentrated and dried over anhydrous MgSO$_4$. The crude 5'-OH product was precipitated from hexane and used in the subsequent coupling reaction without further purification.

B. Coupling of 5'-O-DMT-Monomer synthon of formula III to 5'-OH deprotected dimer, trimer or tetramer The appropriate [Rp] or [Sp] monomer synthon of formula III (3 equivalents) and 5'-OH-deprotected dimer, trimer or tetramer (1 equivalent) were dried twice by coevaporation with dry pyridine and left overnight in a desiccator under high vacuum. To those reagents, LiCl (10 equivalents) was added. The resulting mixture was dissolved in pyridine (to give a 0.1 to 0.2M solution). Then, DBU (10 equivlents) in pyridine was added in one portion. The reaction mixture was kep at room temperature for 0.5 to 1.0 hour, concentrated to about one third of its volume, and the residue was from cold hexane. The corresponding crude product was redissolved in chloroform and the resulting solution was extracted twice with phosphoate buffer (pH 7). Combined organic layers were dried over anhydrous MgSO$_4$, concentrated and purified by mens of column chromatography, eluting with ethanol in chloroform (gradient 5 to 10% ethanol).

Example 61
Preparation of [Rp,Rp]-DMT-C$^{Bz}$$_{PMe}$T$_{PMe}$G$^{ibu}$Ac

The above-identified trimer was prepared using [Rp]HO-5'-thymidyl-(3',5')-N$^4$-isobutyryl-3'-O-acetyl-2'-deoxyguanosine 3'-Methylphosphonate (0.170 g, 0.25 mmol and 1 equivalent) and the [Sp]-5'-O-DMT-N$^4$-Benzoyl-2'-deoxycytidine 3'-O-(Se-methyl methylphosphonoselenoate) of formula III and following the procedures described in Example 60. Yield: 45%. $^{31}$P NMR δ (CDCl$_3$)δ: 32.80, 32.07. $^1$H NMR δ (CDCl$_3$): 1.65 (3H, d, PCH$_3$); $^2$J$_{P-H}$=17.45 Hz. FAB$^-$MS [M-H]: 1373, 1374.

Example 62
Preparation of [Sp,Sp]-DMT-C$^{Bz}$$_{PMe}$T$_{PMe}$G$^{ibu}$-AC

The above-identified trimer was prepared using the corresponding [Sp]HO-5'-thymidyl-(3',5')-N$^4$-isobutyryl-3'-O-acetyl-2'-deoxyguanosine-3'-methylphosphonate (0.27 g, 0.39 mmol, 1 equivalent) and the [Rp]-5-O-DMT-N$^4$-benzoyl-2'-deoxycytidine-3'-O-(Se-methyl methylphosphonoselenoate) of formula III (3 equivalents) and following the procedures of Example 60. The trimer was purified by column chromatography using a gradient 0 to 8% ethanol in chloroform. Yield: 40%. $^{31}$P NMR δ (CDCl$_3$): 33.87, 33.75. $^1$H NMR δ (CDCl$_3$): 1.655 (3H, d, P-CH$_3$), $^2$J$_{P-H}$=17.51 Hz; 1.648 (3H, d, P-CH$_3$); $^2$J$_{P-H}$=17.59 Hz. FAB$^-$MS [M-H]: 1374, 1375.

Example 63
Preparaton of [Rp,Rp,Rp]-DMT-C$^{Bz}$$_{PMe}$C$^{Bz}$$_{PMe}$T$_{PMe}$G$^{ibu}$-Ac The above-identified tetramer was prepared using [Rp, Rp]-HO-5'-C$^{Bz}$$_{PMe}$T$_{PMe}$G$^{ibu}$-AC (0.9 g, 0.084 mmol), 1 equivalent and [Sp]5-O-DMT-N$^4$-benzoyl-2'-deoxycytidine-3-O-(Se-methyl methylphosphonoselenolate) of formula III (3 equivalents) and following the procedures described in Example 60. The tetramer was purified by column chromatography using a gradient of 0 to 10% ethanol in chloroform. Yield: 55%. $^{31}$P NMR δ (CDCl$_3$)δ: 33.72, 33.54, 33.44. $^1$H NMR δ (DMSO-d$_6$): 1.694 (3H, d, P-CH$_3$), $^2$J$_{P-H}$=17.61 Hz; 1.656 (3H, d, P-CH$_3$), $^2$J$_{P-H}$=17.61 Hz; 1.612 (3H, d, P-CH$_3$), $^2$J$_{P-H}$=17.54 Hz. MS FAB-[M-H]: 1763, 1764.

Example 64
Preparation of [Sp,Sp,Sp]-DMT-C$^{Bz}$$_{PMe}$C$^{Bz}$$_{PMe}$T$_{PMe}$G$^{ibu}$-Ac The above-identified tetramer was prepared using [Sp,Sp]-HO-5'-C$^{Bz}$$_{PMe}$-T$_{PMe}$G$^{ibu}$-Ac (0.15 g, 0.14 mmol, 1 equivalent) and [Rp]5'-DMT-N$^4$-benzoyl-2'-deoxycytidine-3'-O-(Se Methyl Methylphosphonoselenoate) of formula III (3 equivalents) and following the procedures described in Example 60. The tetramer was purified by column chromatography using a gradient of 0 to 10% ethanol in chloroform. Yield: 40%. $^{31}$P NMR δ (CDCl$_3$): 33.72, 33.54, 33.44. $^1$H NMR δ (pyridine-d$_5$): 1.751, 1.735, 1.717, 1.698, 1.674 (P-CH$_3$). MS$^-$FAB [M-H]: 1763, 1764.

Example 65

Preparation of [Rp, Rp, Rp, Rp]-DMT-T$_{PMe}$C$^{Bz}_{PMe}$C$^{Bz}_{PMe}$T$_{PMe}$G$^{ibu}$-Ac The above-identified tetramer was prepared using [Rp, Rp,Rp] HO-5'-C$^{Bz}_{PMe}$-C$^{Bz}_{PMe}$T$_{PMe}$G$^{ibu}$-AC (0.025 g, 0.017 mmol, 1 equivalent) and [Sp]-5'-O-DMT-thymidine-3'-O-(S-methyl-methylphosphonoselenoate) of formula III (3 equivalents) and following the procedures of Example 60. The resulting pentamer was purified by column chromatography using a gradient of 0 to 14% ethanol in chloroform. Yield: 40%. $^{31}$P NMR δ (DMSO-d$_6$): 32.72, 32.82, 32.22 (double intensity). FAB$^-$MS: 2024, 2025 (M-Ac).

Example 66

Preparation of [Sp,Sp,Sp,Sp]-DMT-T$_{PMe}$-C$^{Bz}_{PMe}$-C$^{Bz}_{PMe}$-T$_{PMe}$-G$^{ibu}$-Ac The above-identified pentamer was prepared using [Sp, Sp,Sp]-HO-5'-C$^{Bz}_{PMe}$-C$^{Bz}_{PMe}$T$_{PMe}$G$^{ibu}$-Ac (0.055 g., 0.04 mmol, 1 equivalent) and [Rp]-5'O-DMT-Thymidine-3'-O-(Se-methyl-methylphosphonoselenoate) of formula III (3.50 equivalents) and following the procedures described in Example 60. The resulting pentamer was purified by column chromatography using a gradient of 0 to 18% ethanol in chloroform. Yield: 40%. $^{31}$P NMR δ (pyridine-d$_5$-MeOH, 2:3 v/v): 34.22 (double intensity), 34.28, 34.37. FAB$^-$MS: 2025, 2026 [M-Ac-1], FAB$^+$MS: 2027, 2028 {M-Ac+1]; 2089, 2090 {M+Na}.

Example 67

General Procedure for Deprotection of Trimers, Tetramers and Pentamers

A. Removal of Base-Labile Protecting Groups

Fully protected trimer, tetramer or pentamer (2 mg) was dissolved in a solution of NH$_4$OH-MeCN-ETOH (10:45:45) (1 mL) and kept at room temperature for 0.5 hours. Ethylene diamine (1 mL) was added to this solution and stirring was continued for an additional 6 hours. Solvents and reagents were removed by evaporation under reduced pressure. The residue was coevaportaed twice with absolute ethanol.

B. Removal of (4,4'-Dimethoxytrityl)-Protecting Group

Partially protected product from step (A) was dissolved in 80% acetic acid (1 mL) and kept at room temperature for 30 minutes. The reaction mixture was concentrated to dryness. Then, the residue was coevaporated twice with absolute ethanol, and washed with diethyl ether and redissolved in H$_2$O-MeCN (1:1). The product was analyzed by RP-HPLC (ODS-Hypersil, 5 μm, 25 cm).

We claim:

1. A method for the synthesis of chirally pure nucleoside dimers of chosen sense of P-chirality of the formula:

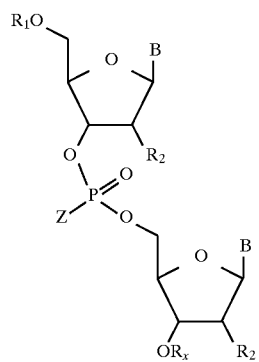

wherein
(a) R$_2$ is a protecting group;
(b) each R$_2$ is independently selected from hydrogen, optionally protected hydroxy, halogen, chloroalkyl or fluoroalkyl of 1 to 12 carbon atoms and 1 to 9 chlorine or fluorine atoms, cyano, azido, optionally protected amino, perfluoroalkyl of 1 to 4 carbon atoms, perfluoroalkoxy of 1 to 4 carbon atoms, alkoxyalkyl, vinyl, ethynyl -Q$_1$, -OQ$_1$, -SQ$_1$ or -NHQ$_1$ wherein Q$_1$ is alkyl of 1 to 12 carbon atoms, aryl of 1 to 12 carbon atoms, aralkyl of 2 to 15 carbon atoms, alkaryl of 2 to 15 carbon atoms, alkenyl of 3 to 12 carbon atoms, and alkynyl of 3 to 12 carbon atoms;
(c) B is an independently selected optionally protected nucleoside base;
(d) Z is independently selected from -Q$_1$, vinyl, ethynyl, optionally protected aminomethyl and optionally protected aminoethyl; and
(e) R$_X$ is an aroyl protecting group, acyl protecting group, alkoxycarbonyl protecting group, benzenesulfonyl or ring-substituted benzenesulfonyl protecting group, a coupling group, a silyl protecting group, a 5'-O-nucleotide analog or a 5'-O-oligonucleotide analog or an alkyl protecting group;

which comprises
(i) separating a racemic mixture of the compound of formula (II)

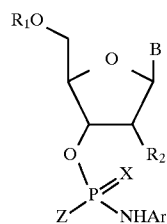

into diastereomers of chosen and unchosen sense of P-chirality, wherein X is sulfur or selenium, Ar is phenyl optionally substituted with 1 to 5 substitutients independently selected from halogen, nitro, cyano and lower alkyl;
(ii)
(a) contacting the diastereomer of the chosen sense of P-chirality with a strong non-nucleophilic base and carbon dioxide to give a transient nucleoside 3'-O-(Z-substituted) phosphonoselenoic or phosphonothioic acid intermediate;
(b) contacting the transient intermediate of step (ii)(a) with an alkylating agent of the formula R$_3$W wherein W is chloro, bromo, iodo, alkanesulfonyl, perfluoroalkanesulfonyl, triflate, tosylate, mesitylate, triisopropyl benzenesulfonyl or benzenesulfonyl and $R_3$ is $-Q_1$ to give a chirally pure diastereomer of the chosen sense of P-chirality of the formula (III)

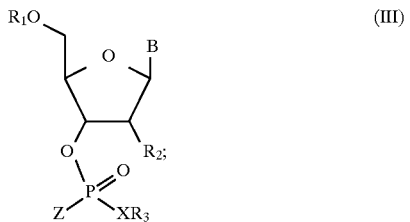

(iii) contacting the diastereomer of the unchosen sense of P-chirality from step (i) with an oxygen transferring oxidizing agent to form an intermediate nucleoside of the unchosen sense of P-chirality of the formula (IV)

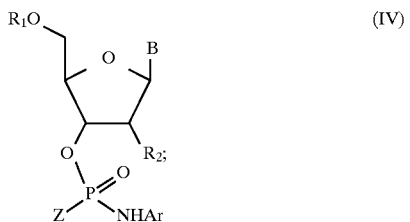

(iv)
(a) contacting the intermediate nucleoside of step (iii) with a strong non-nucleophilic base and $CX_2$ to give a transient nucleoside 3'-O-(Z-substituted) phosphonoselenoic or phosphonothioic acid intermediate; and (b) contacting the transient intermediate of step (iv)(a) with an alkylating agent of the formula $R_3W$ to give a diastereomer of the chosen sense of P-chirality of formula (III); and (v) coupling the diastereomer of formula (III) with a nucleoside of formula (V)

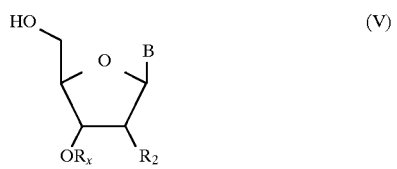

under stereospecific coupling conditions including DBU and a Lithium halide to give the chirally pure dimer of chosen sense of P-chirality of formula I.

2. A method according to claim 1 wherein said oxygen transferring oxidizing reagent is selected from the group consisting of oxone, hydroperoxide, alkylhydroperoxides, arylhydroperoxide, perbenzoic acids, and perphthalates.

3. A method for the synthesis of chirally pure nucleoside monomer synthons of chosen sense of P-chirality of the formula III:

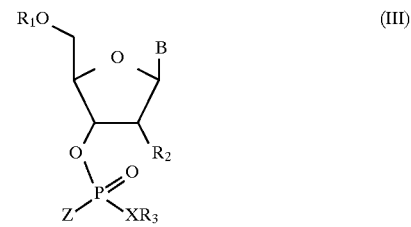

wherein
(a) $R_1$ is a protecting group;
(b) each $R_2$ is independently selected from hydrogen, optionally protected hydroxy, halogen, chloroalkyl or fluoroalkyl of 1 to 4 carbon atoms and 1 to 9 chlorine or fluorine atoms, cyano, azido, optionally protected amino, perfluoroalkyl of 1 to 4 carbon atoms, perfluoroalkoxy of 1 to 12 carbon atoms, alkoxyalkyl, vinyl, ethynyl $-Q_1$, $-OQ_1$, $-SQ_1$ or $-NHQ_1$ wherein $Q_1$ is alkyl of 1 to 12 carbon atoms, aryl of 1 to 12 carbon atoms, aralkyl of 2 to 15 carbon atoms, alkaryl of 2 to 15 carbon atoms, alkenyl of 3 to 12 carbon atoms, and alkynyl of 3 to 12 carbon atoms;

(c) B is an independently selected optionally protected nucleoside base;

(d) Z is independently selected from $-Q_1$, vinyl, ethynyl, optionally protected aminomethyl and optionally protected aminoethyl;

(e) $R_3$ is $-Q_1$; and (f) X is selenium or sulfur;

which comprises
(i) separating a racemic mixture of the compound of formula (II)

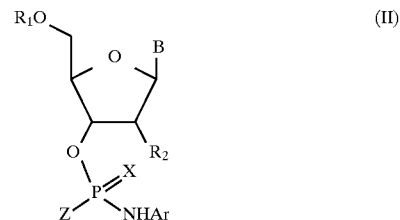

into diasteromers of chosen and unchosen sense of P-chirality, wherein Ar is phenyl optionally substituted with 1 to 5 substitutients independently selected from halogen, nitro, cyano and lower alkyl;

(ii)
(a) contacting the diastereomer of the chosen sense of P-chirality with a strong non-nucleophilic base and carbon dioxide to give a transient nucleoside 3'-O-(Z-substituted) phosphonoselenoic or phosphonothioic acid intermediate;

(b) contacting the transient intermediate of step (ii)(a) with an alkylating agent of the formula $R_3W$ wherein W is chloro, bromo, iodo, alkanesulfonyl, perfluoroalkanesulfonyl, triflate, tosylate, mesitylate, triisopropyl benzenesulfonyl or benzenesulfonyl to give a chirally pure diastereomer of the chosen sense of P-chirality of the formula (III)

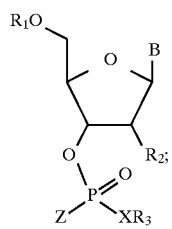

(III)

(iii) contacting the diastereomer of the unchosen sense of P-chirality from step (i) with an oxygen transferring oxidizing agent to form an intermediate nucleoside of the unchosen sense of P-chirality of the formula (IV)

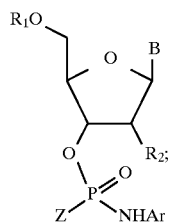

(IV)

(iv)
(a) contacting the intermediate nucleoside of step (iii) with a strong non-nucleophilic base and $CX_2$ to give a transient nucleoside 3'-O-(Z-substituted) phosphonoselenoic or phosphonothioic acid intermediate; and
(b) contacting the transient intermediate of step (iv) (a) with an alkylating agent of the formula $R_3W$ to give a chirally pure diastereomer of the chosen sense of P-chirality of formula (III).

4. A method according to claim 3 wherein said oxygen transferring oxidizing agent is selected from the group consisting of oxone, hydroperoxides, alkylhydroperoxides, arylhydroperoxides, perbenzoic acids and perphthalates.

5. A method for the synthesis of chirally pure nucleoside monomer synthons of chosen sense of P-chirality of the formula III:

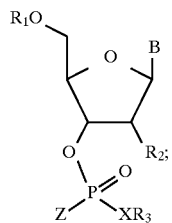

(III)

wherein
(a) $R_1$ is a protecting group;
(b) each $R_2$ is independently selected from hydrogen, optionally protected hydroxy, halogen, chloroalkyl or fluoroalkyl of 1 to 4 carbon atoms and 1 to 9 chlorine or fluorine atoms, cyano, azido, optionally protected amino, perfluoroalkyl of 1 to 4 carbon atoms, perfluoroalkoxy of 1 to 4 carbon atoms, alkoxyalkyl, vinyl, ethynyl -$Q_1$, -$OQ_1$, -$SQ_1$ or -$NHQ_1$ wherein $Q_1$ is alkyl of 1 to 12 carbon atoms, aryl of 1 to 12 carbon atoms, aralkyl of 2 to 15 carbon atoms, alkaryl of 2 to 12 carbon atoms, alkenyl of 3 to 12 carbon atoms, and alkynyl of 3 to 12 carbon atoms;
(c) B is an independently selected optionally protected nucleoside base;
(d) Z is independently selected from -$Q_1$, vinyl, ethynyl, optionally protected aminomethyl and optionally protected aminoethyl;

(e) $R_3$ is -$Q_1$; and
(f) X is selenium or sulfur; which comprises
(i) separating a racemic mixture of the compound of formula (II)

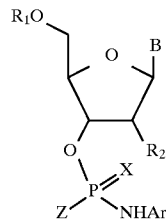

(II)

into diastereomers of chosen and unchosen sense of P-chirality, wherein Ar is phenyl optionally substituted with 1 to 5 substitutients independently selected from halogen, nitro, cyano and lower alkyl;
(ii)
(a) contacting the diastereomer of the chosen sense of P-chirality a strong non-nucleophilic and carbon dioxide to give a transient nucleoside 3'-O-(Z-substituted) phosphonoselenoic or phosphonothioic acid intermediate; and
(b) contacting the transient intermediate of step (ii)(a) with an alkylating agent of the formula $R_3W$ wherein W is chloro, bromo, iodo, alkanesulfonyl, perfluoroalkanesulfonyl, triflate, tosylate, mesylate, triisopropyl benzenesulfonyl or benzenesulfonyl to give a chirally pure diastereomer of the chosen sense of P-chirality of the formula (III)

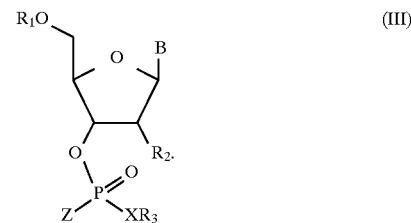

(III)

6. A method for the synthesis of chirally pure nucleoside monomer synthons of chosen sense of P-chirality of the formula III:

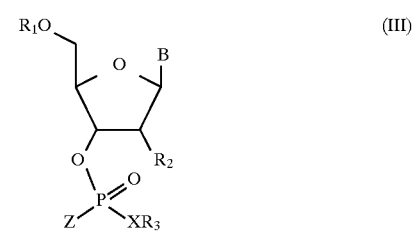

(III)

wherein
(a) $R_1$ is a protecting group;
(b) each $R_2$ is independently selected from hydrogen, optionally protected hydroxy, halogen, chloroalkyl or fluoroalkyl of 1 to 4 carbon atoms and 1 to 9 chlorine or fluorine atoms, cyano, azido, optionally protected amino, perfluoroalkyl of 1 to 4 carbon atoms, perfluoroalkoxy of 1 to 4 carbon atoms, alkoxyalkyl, vinyl, ethynyl -$Q_1$, -$OQ_1$, -$SQ_1$ or -$NHQ_1$ wherein $Q_1$ is alkyl of 1 to 12 carbon atoms, aryl of 1 to 12 carbon atoms, aralkyl of 2 to 15 carbon atoms, alkaryl of 2 to 15 carbon atoms, alkenyl of 3 to 12 carbon atoms, and alkynyl of 3 to 12 carbon atoms;

(c) B is an independently selected optionally protected nucleoside base;

(d) Z is independently selected from $-Q_1$, vinyl, ethynyl, optionally protected aminomethyl and optionally protected aminoethyl;

(e) $R_3$ is $-Q_1$; and (f) X is selenium or sulfur; which comprises (i) separating a racemic mixture of the compound of formula (II)

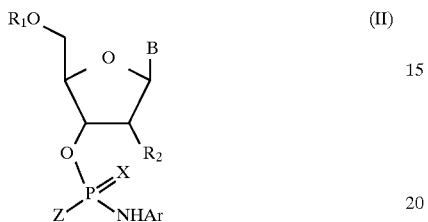

(II)

into diasteromers of chosen and unchosen sense of P-chirality, wherein X is sulfur or selenium, Ar is phenyl optionally substituted with 1 to 5 substitutients independently selected from halogen, nitro, cyano and lower alkyl;

(ii) contacting the diastereomer of the unchosen sense of P-chirality from step (i) with an oxygen transferring oxidizing agent to form an intermediate nucleoside of the unchosen sense of P-chirality of the formula (IV)

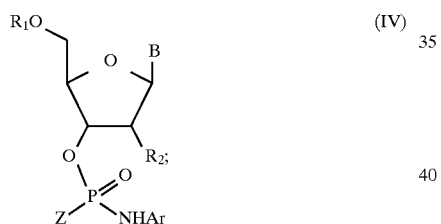

(IV)

(iii)

(a) contacting the intermediate nucleoside of step (ii) with a strong non-nucleophilic base and $CX_2$ to give a transient nucleoside 3'-O-(Z-substituted) phosphonoselenoic or phosphonothioic acid intermediate; and (b) contacting the transient intermediate of step (iii)(a) with an alkylating agent of the formula $R_3W$ wherein W is chloro, bromo, iodo, alkanesulfonyl, perfluoroalkanesulfonyl, triflate, tosylate, mesitylate, triisopropyl benzenesulfonyl, or benzenesulfonyl to give a chirally pure diastereomer of the chosen sense of P-chirality of formula (III).

7. A method according to claim 6 wherein said oxygen transferring oxidizing agent is selected from the group consisting of oxone, hydroperoxide, alkylhydroperoxides, arylperoxides, perbenzoic acids and perphthalates.

8. A method of converting a nucleoside monomer intermediate of unchosen sense of P-chirality of formula (II) to a nucleoside monomer synthon of chosen sense of P-chirality of the formula (III)

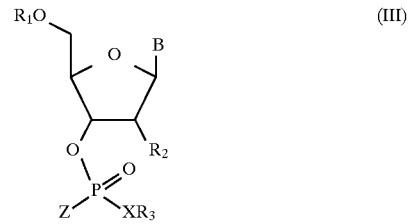

(III)

wherein (a) $R_1$ is a protecting group;

(b) each $R_2$ is independently selected from hydrogen, optionally protected hydroxy, halogen, chloroalkyl or fluoroalkyl of 1 to 4 carbon atoms and 1 to 9 chlorine or fluorine atoms, cyano, azido, optionally protected amino, perfluoroalkyl of 1 to 4 carbon atoms, perfluoroalkoxy of 1 to 4 carbon atoms, alkoxyalkyl, vinyl, ethynyl $-Q_1$, $-OQ_1$, $-SQ_1$ or $-NHQ_1$ wherein $Q_1$ is alkyl of 1 to 12 carbon atoms, aryl of 1 to 12 carbon atoms, aralkyl of 2 to 15 carbon atoms, alkaryl of 2 to 15 carbon atoms, alkenyl of 3 to 12 carbon atoms, and alkynyl of 3 to 12 carbon atoms;

(c) B is an independently selected optionally protected nucleoside base;

(d) Z is independently selected from $-Q_1$, vinyl, ethynyl, optionally protected aminomethyl and optionally protected aminoethyl; and (e) $R_3$ is $-Q_1$; and (f) X is selenium or sulfur;

which comprises (i) contacting a diastereomer of the unchosen sense of P-chirality of formula II

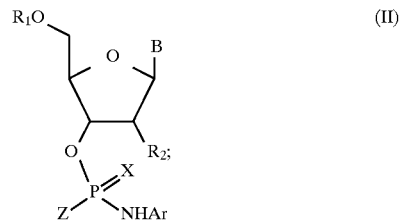

(II)

wherein X is sulfur or selenium and Ar is phenyl optionally substituted with 1 to 5 substitutients independently selected from halogen, nitro, cyano and lower alkyl with an oxygen transferring oxidizing agent to form a second intermediate nucleoside of the unchosen sense of P-chirality of the formula (IV)

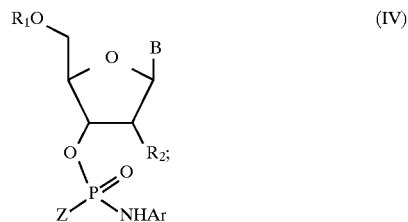

(IV)

(ii)

(a) contacting the intermediate nucleoside of step (i) with strong non-nucleophilic base and $CX_2$ to give a transient nucleoside 3'-O-(Z-substituted) phosphonoselenoic or phosphonothioic acid intermediate; and (b) contacting the transient intermediate of step (ii)(a) with an alkylating agent of the formula $R_3W$ wherein W is chloro, bromo, iodo, alkanesulfonyl, perfluoroalkanesulfonyl, triflate, tosylate, mesitylate, triisoprophylbenzenesulfonyl or benzenesulfonyl, to give a diastereomer of the chosen sense of P-chirality of formula (III).

9. A method according to claim 8 wherein said oxygen transferring oxidizing agent is selected from the group consisting of oxone, hydroperoxide, alkylhydroperoxides, arylperoxides, perbenzoic acids and perphthalates.

10. A method according to any one of claims 1, 3, 5, 6 or 8 wherein said strong non-nucleophilic base is selected from sodium hydride and DBU.

11. A compound of the formula II

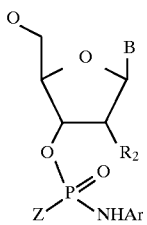

wherein (a) $R_1$ is a protecting group, (b) each $R_2$ is independently selected from hydrogen, optionally protected hydroxy, halogen, chloroalkyl or flouroalkyl of 1 to 4 carbon atoms and 1 to 9 chlorine or fluorine atoms, cyano, axido, optionally protected amino, perfluoroalkyl of 1 to 4 carbon atoms, perfluoroalkoxy of 1 to 4 carbon atoms, perfluoroalkoxy of 1 to 4 carbon atoms, alkoxyalkyl, vinyl, ethynyl -Q, -$OQ_1$, -$SQ_1$ or $NHQ_1$ wherein $Q_1$ is alkyl of 1 to 12 carbon atoms, aryl of 1 to 12 carbon atoms, aralkyl of 2 to 15 carbon atoms, alkaryl of 2 to 15 carbon atoms, alkenyl of 3 to 12 atoms, and alkynyl of 3 to 12 carbon atoms; (c) B is an independently selected optionally protected nucleoside base; (d) Z is independently selected from -$Q_1$, vinyl, ethynyl, optionally protected aminomethyl and optionally protected aminoethyl; (e) X is sulfur or selenium; and (f) Ar is phenyl optionally substituted with 1 to 5 substututients independently selected from halogen, nitro, and lower alkyl of 1 to 6 carbon atoms, with the proviso that when $R_2$ is hydrogen, optionally protected hydroxyl or methoxy, then Ar is not unsubstituted phenyl.

12. A compound of the formula III

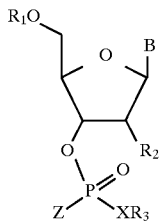

wherein (a) $R_1$ is a protecting group, (b) each $R_2$ is independently selected from hydrogen, optionally protected hydroxy, halogen, chloroalkyl or fluoroalkyl of 1 to 4 carbon atoms and 1 to 9 chlorine or fluorine atoms, cyano, azido, optionally protected amino, perfluoroalkyl of 1 to 4 carbon atoms, perfluoroalkoxy of 1 to 4 carbon atoms, alkoxyalkyl, vinyl, ethynyl -$Q_1$, -$OQ_1$, -$SQ_1$ or -$NHQ_1$ wherein $Q_1$ is alkyl of 1 to 12 carbon atoms, aryl of 1 to 12 carbon atoms, aralkyl of 2 to 15 carbon atoms, alkaryl of 2 to 15 carbon atoms, alkenyl of 3 to 12 carbon atoms, and alkynyl of 3 to 12 carbon atoms; (c) B is an independently selected optionally protected nucleoside base; (d) Z is independently selected from -$Q_1$, vinyl, ethynyl, optionally protected aminomethyl and optionally protected aminoethyl; (e) $R_3$ is -$Q_1$; and (f) X is selenium or sulfur, with the proviso that when $R_2$ is hydrogen, optionally protected hydroxyl or methoxy then $R_3$ is not methyl, benzyl or nitrobenzyl.

13. A compound of the formula IV:

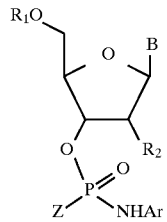

wherein (a) $R_1$ is a protecting group; (b) each $R_2$ is independently selected from hydrogen, optionally protected hydroxy, halogen, chloroalkyl or fluoroalkyl of 1 to 4 carbon atoms and 1 to 9 chlorine or fluorine atoms, cyano, azido, optionally protected amino, perfluoroalkyl of 1 to 4 carbon atoms, perfluoroalkoxy of 1 to 4 carbon atoms, alkoxyalkyl, vinyl, ethynyl -$Q_1$, -$OQ_1$, -$SQ_1$ or -$NHQ_1$ wherein $Q_1$ is alkyl of 1 to 12 carbon atoms, aryl of 1 to 12 carbon atoms, aralkyl of 2 to 15 carbon atoms, alkaryl of 2 to 15 carbon atoms, alkenyl of 3 to 12 carbon atoms, and alkynyl of 3 to 12 carbon atoms; (c) B is an independently selected optionally protected nucleoside base; (d) Z is independently selected from -$Q_1$, vinyl, ethynyl, optionally protected aminomethyl and optionally protected aminoethyl; and (e) Ar is phenyl optionally substituted with 1 to 5 substitutents independently selected from halogen, nitro, cyano and lower alkyl of 1 to 6 carbon atoms.

14. A compound of any one of claims 11, 12 or 13 wherein Z is selected from lower alkyl of 1 to 4 carbon atoms, optionally protected aminomethyl or optionaly protected aminoethyl.

15. A compound according to claim 14 wherein $R_2$ is selected from hydrogen, optionally protected hydroxyl, halogen, optionally protected amino, azido, cyano, alkoxyalkyl, vinyl, -$Q_1$, -$OQ_1$, -$SQ_1$, or -$NHQ_1$, wherein $Q_1$ is lower alkyl of 1 to 4 carbon atoms or alkenyl of 3 to 4 carbon atoms.

16. A compound according to claim 12 wherein X is sulfur.

* * * * *